US007687457B2

(12) United States Patent
Craik et al.

(10) Patent No.: US 7,687,457 B2
(45) Date of Patent: Mar. 30, 2010

(54) CYCLIC MOLECULAR FRAMEWORK AND DERIVATIVES THEREOF

(75) Inventors: David James Craik, Chapel Hill (AU); Norello Lee Daly, St. Lucia (AU); Clements Waim-Kunduane Waine, Port Moresby (PG)

(73) Assignee: The University of Queensland (AU)

( * ) Notice: Subject to any disclaimer, the term of this patent is extended or adjusted under 35 U.S.C. 154(b) by 0 days.

(21) Appl. No.: 11/120,501

(22) Filed: May 3, 2005

(65) Prior Publication Data

US 2006/0035819 A1    Feb. 16, 2006

Related U.S. Application Data

(63) Continuation of application No. 10/121,282, filed on Apr. 12, 2002, now abandoned, which is a continuation of application No. PCT/AU00/01248, filed on Oct. 13, 2000.

(30) Foreign Application Priority Data

Oct. 13, 1999    (AU) .................................. PQ3398

(51) Int. Cl.
C07K 14/00    (2006.01)
C07K 1/04    (2006.01)
A61K 38/16    (2006.01)
(52) U.S. Cl. .............................. 514/9; 514/12; 530/300; 530/317; 530/370; 530/334; 530/335; 530/344
(58) Field of Classification Search ..................... 514/9, 514/12; 530/317, 300, 370, 334, 344, 335
See application file for complete search history.

(56) References Cited

FOREIGN PATENT DOCUMENTS

WO     WO 99/00406     1/1999
WO     WO 99/54358     10/1999
WO     WO/00/68265 A   11/2000

OTHER PUBLICATIONS

Tam et al. , Proc. Natl. Acad. Sci. USA 96, 8913-8918 (Aug. 1999).*
Vita et al., Proc. Natl. Acad. Sci. USA 92, 6404-6408 (Jul. 1995).*
Database PBD, Jan. 13, 1995. XP002351103, PDB Accession No. 1KAL.
Derua, Rita et al., Sep. 30, 1996. XP002351615, "Analysis of the dislulfide linkage pattern in circulin A and B, HIV-inhibitory macrocyclic peptides"Biochemical and Biophysical Research Communications vol. 228, pp. 632-638.
Daly, N. L., A. Koltay and D. J. Craik, Jun. 12, 1998. XP002351099, "Circulin A from Chassalia Parviflora, NMR, 12 Structures." Database PDB Accession No. 1BH4.
Craik, D. J. et al., Dec. 17, 1999, "Plant Cyclotides: A Unique Family of Cyclic and Knotted Proteins that Defines the Cyclic Cystune Knot Structural Motif." Journal of Molecular Biology. 1327-1336.
Database UniProt 'Online!, May 30, 2000, "Circulin A (CIRA.)" XP002351100, EBI Accession No. Uniprot: Cira-Chapa.
Database EPO Proteins 'Online!, Dec. 15, 2000, "Sequence 10 from Patent W00068265." XP002351102, EBI Accession No. EPOP: AX047096.
Database UniProt, Feb. 28, 2003, "Cycloviolacin 05", XP002351101, UniProt Accession No. CY05-VI00D.
Chemical Abstracts 112:116819 (J. Siekmann et al., Biol. Chem. Hoppe-Seyler, 370(7), pp. 677-681 (1989)).
Chemical Abstracts 121:200908 (K.R. Gustafson et al., J. Am. Chem. Soc., 116(20) pp. 9337-9338 (1994)).
Chemical Abstracts 122:156318 (K.M. Witherup et al., J. Nat. Prod., 57(12), pp. 1619-1625 (1994)).
Chemical Abstracts 126:26370 (R. Derua et al., Biochem. Biophys. Res. Commun., 228(2), pp. 632-638 (1996)).
J.P. Tam et al., Protein Sci., 7(7), pp. 1583-1592 (1998).
Chemical Abstracts 130:264790 (V. Goeransson et al., J. Nat. Prod., 62(2), pp. 283-286 (1999)).
J.P. Tam et al., J. Am. Chem. Soc., 121(18), pp. 4316-4324 (1999).
Chemical Abstracts 131:243565 (N.L. Daly et al., Biochemistry, 38(32), pp. 10606-10614 (1999).
J.P. Tam et al., Proc. Natl. Acad. Sci. USA, 96, pp. 8913-8918 (Aug. 1999).
Chemical Abstracts 122:25598 (P.K. Pallaghy et al., Protein Sci., 3(10), pp. 1833-1836 (1994)).
Hernandez JF et al., 2000, "Squash Trypsin Inhibitors from *Momordica cochinchinensis* Exhibit an Atypical Macrocyclic Structure" *Biochemistry*, 39:5722-5730.
Daly NL et al., 1999, "Solution Structure by NMR of Circulin A: A Macrocyclic Knotted Peptide Having Anti-HIV Activity" *J. Mol. Biol.*, 285:333-345.
Daly NL et al., 1999, "Chemical Synthesis and Folding Pathways of Large Cyclic Polypeptides: Studies of the Cystine Knot Polypeptide Kalata B1" *Biochemistry*, 38:10606-10614.
Oosterom J et al., 1999, "Conformation of the Core Sequence in Melanocortin Peptides Directs Selectivity for the Melanocortin MC3 and MC4 Receptors" *J. Biol. Chem.*, 274(24):16853-16860.
Göranswson U et al., 1999, Seven Novel Macrocyclic Polypeptides from *Viola arvensis*, *J. Nat. Prod.*, 62:283-286.
Murthy Krishna HM et al., 1999, "Dengue Virus NS3 Serine Protease" *J. Biol. Chem.*, 274(9):5573-5580.
Claeson P et al., 1998, "Fractionation Protocol for the Isolation of Polypeptides from Plant Biomass" *J. Nat. Prod.*, 61:77-81.
Norton RS et al., 1998, "The Cystine Knot Structure Of Ion Channel Toxins and Related Polypeptides" *Toxicon*, 36(11):1573-1583.

(Continued)

*Primary Examiner*—Chih-Min Kam
(74) *Attorney, Agent, or Firm*—Casimir Jones, S.C.

(57) ABSTRACT

The present invention relates generally to a molecular framework having a cyclic structure. More particularly, the present invention provides cyclic proteins and derivatives thereof in which particular turns and other elements of the molecular structure are held in defined orientations with respect to each other. The cyclic proteins of the present invention provide a molecular framework for the introduction of particular amino acids or heterologous amino acid sequences to facilitate the presentation of biological activities associated with these heterologous amino acid sequences. The molecular framework of the present invention may be naturally cyclic or may be a cyclized derivative of a linear molecular or may be a linear derivative of a cyclized molecule. The present invention contemplates the use of the molecular framework with or without particular amino acids inserted or substituted thereon for the treatment of or prophylaxis of disease conditions in animals, mammals (including humans) and plants.

9 Claims, 8 Drawing Sheets

OTHER PUBLICATIONS

Vervoot J et al., 1997, "The race-specific elicitor AVR9 of the tomato pathogen *Cladosporium fulvum*: a cystine knot protein" *Febs Letters*, 404:153-158.

Nielsen KJ et al., 1996, "A Consensus Structure for ω-Conotoxins with Different Selectivities for Voltage-sensitive Calcium Channel Subtypes: Comparison of MVIIA, SVIB and SNX-202" *J. Mol. Biol.*, 263:297-310.

Broekaert WF et al., 1995, "Plant Defensins: Novel Antimicrobial Peptides as Components of the Host Defense System" *Plant Physiol.*, 108:1353-1358.

Chen W et al., 1995, "A Colorimetric Assay for Measuring Activation of $G_s$- and $G_q$-Coupled Signaling Pathways" *Analytical Biochemistry*, 226:349-354.

Issacs NW, 1995, "Cystine Knots" *Current Opinion in Structural Biology*, 5:391-395.

Saether O et al., 1995, "Elucidation of the Primary and Three-Dimensional Structure of the Uterotonic Polypeptide Kalata B1" *Biochemistry*, 34:4147-4158.

Gustafson KR et al., 1994, "Circulins A and B: Novel HIV-Inhibitory Macrocyclic Peptides from the Tropical Tree *Chassalia parvifolia*" *J. Am. Chem. Soc.*, 116:9337-9338.

Narqsimham et al., 1994, "Snail and spider toxins share a similar tertiary structure and 'cystine motif'" *Structural Biology*, 1(12):850-852.

Pallaghy PK et al., 1994, "A common structural motiff incorporating a cystine knot and a triple-stranded β-sheet in toxic and inhibitory polypeptides" *Protein Science*, 3:1833-1839.

Witherup KM et al., 1994, "Cyclopsychotride A, A Biologically Active, 31-Residue Cyclic Peptide Isolated From *Psychotria Longipes*" *Journal of Natural Products*, 57(12):1619-1625.

Benham CJ et al., 1993, "Disulfide bonding patterns and protein topologies" *Protein Science*, 2:41-54.

McDonald NQ et al., 1993, "A Structural Superfamily of Growth Factors Containing a Cystine Knot Motif" *Cell*, 73:421-424.

Murray-Rust JM et al., 1993, "Topological similarities in TGF-β2, PDGF-BB and NGF define a superfamily of polypeptide growth factors" *Current Biology*, 1:153-159.

Schöpke MI et al., 1993, Hämolytisch aktive Komponenten aus *Viola tricolor* L. und *Viola arvensis* Murray *Sci. Pharm.*, 61:145-153.

Schnölzer M et al., 1992, "In situ neutralization in Boc-chemistry solid phase peptide synthesis" *Int . J. Protein Res.*, 40:180-193.

Favel A et al., 1989, "Protease inhibitors from *Ecballium elaterium* seeds" *Int J. Peptide Protein Res.* 33:202-208.

Olivera BM et al., 1987, "Neuronal Calcium Channel Antagonists.. Discrimination between Calcium Channel Subtypes Using ω-Conotoxin from *Conus magus* Venom" *Biochemistry*, 26:2086-2090.

Wüthrich K, 1984, "Polypeptide Secondary Structures in Proteins by NMR," Chapter 9, *NMR of Proteins and Nucleic Acids*, Wiley and Sons, New York.

Cruz LJ et al., 1986, "Calcium Channel Antagonists" *J. Biol. Chem.* 261(14):6230-6233.

Kohler et al., 1975, "Continuous Cultures of fused cells secreting antibody of predefined specificity," *Nature*, 256:495-499.

\* cited by examiner

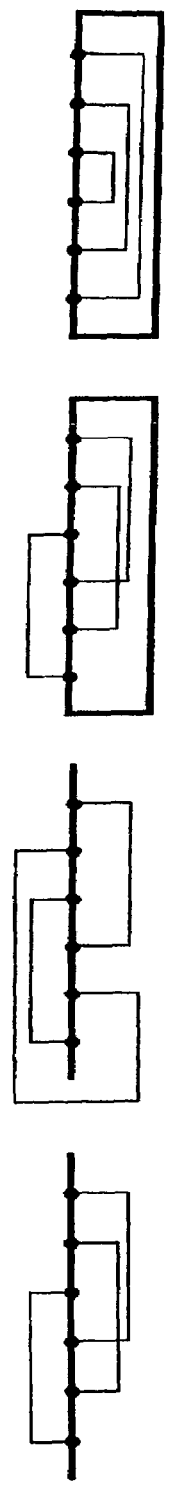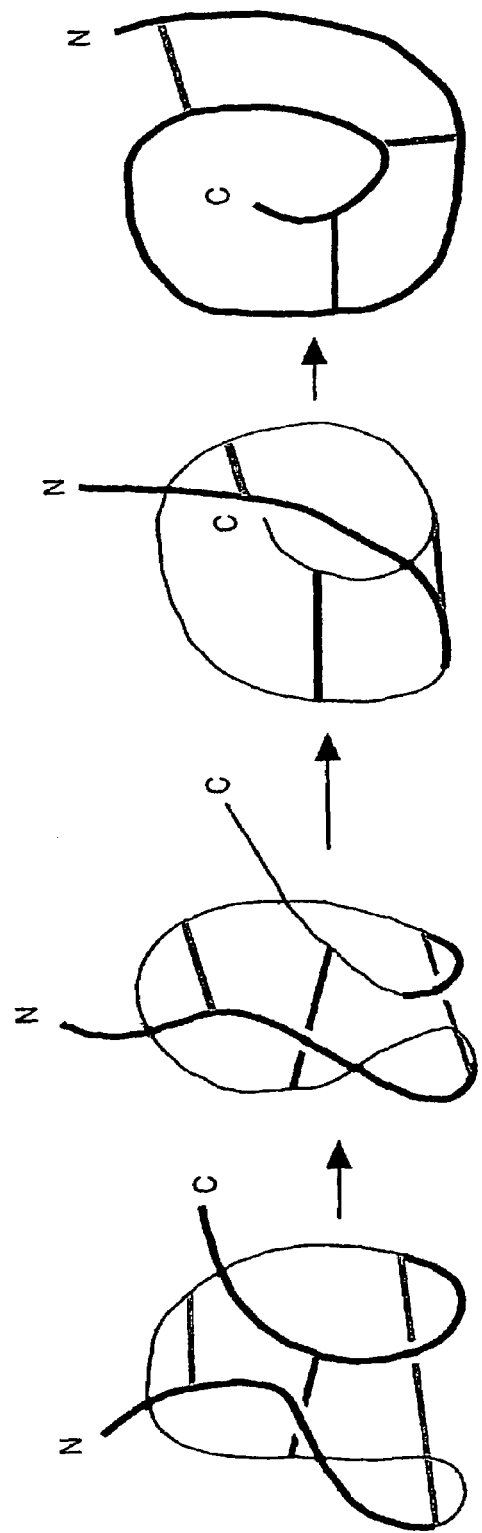
Figure 3a  Figure 3b  Figure 3c  Figure 3d
Figure 3e  Figure 3f  Figure 3g  Figure 3h

SEQUENCE LISTING

<160> NUMBER OF SEQ ID NOS: 47

<210> SEQ ID NO 1
<211> LENGTH: 30
<212> TYPE: PRT

<213> ORGANISM: Viola odorata
<220> FEATURE:
<223> OTHER INFORMATION: cycloviolacin 01

<400> SEQUENCE: 1

Cys Ala Glu Ser Cys Val Tyr Ile Pro Cys Thr Val Thr Ala Leu Leu
1               5                   10                  15

Gly Cys Ser Cys Ser Asn Arg Val Cys Tyr Asn Gly Ile Pro
            20                  25                  30

<210> SEQ ID NO 2
<211> LENGTH: 30
<212> TYPE: PRT
<213> ORGANISM: Viola odorata
<220> FEATURE:
<223> OTHER INFORMATION: cycloviolavin 02

<400> SEQUENCE: 2

Cys Gly Glu Ser Cys Val Trp Ile Pro Cys Ile Ser Ser Ala Ile Gly
1               5                   10                  15

Cys Ser Cys Lys Ser Lys Val Cys Tyr Arg Asn Gly Ile Pro
            20                  25                  30

<210> SEQ ID NO 3
<211> LENGTH: 30
<212> TYPE: PRT
<213> ORGANISM: Viola odorata
<220> FEATURE:
<223> OTHER INFORMATION: cycloviolacin 03

<400> SEQUENCE: 3

Cys Gly Glu Ser Cys Val Trp Ile Pro Cys Leu Thr Ser Ala Ile Gly
1               5                   10                  15

Cys Ser Cys Lys Ser Lys Val Cys Tyr Arg Asn Gly Ile Pro
            20                  25                  30

<210> SEQ ID NO 4
<211> LENGTH: 30
<212> TYPE: PRT
<213> ORGANISM: Viola odorata
<220> FEATURE:
<223> OTHER INFORMATION: cycloviolacin 04

<400> SEQUENCE: 4

Cys Gly Glu Ser Cys Val Trp Ile Pro Cys Ile Ser Ser Ala Ile Gly
1               5                   10                  15

Cys Ser Cys Lys Asn Lys Val Cys Tyr Arg Asn Gly Ile Pro
            20                  25                  30

<210> SEQ ID NO 5
<211> LENGTH: 30
<212> TYPE: PRT
<213> ORGANISM: Viola odorata
<220> FEATURE:
<223> OTHER INFORMATION: cycloviolacin 05

<400> SEQUENCE: 5

Cys Gly Glu Ser Cys Val Trp Ile Pro Cys Ile Ser Ser Ala Val Gly
1               5                   10                  15

Cys Ser Cys Lys Asn Lys Val Cys Tyr Lys Asn Gly Thr Pro
            20                  25                  30

<210> SEQ ID NO 6
<211> LENGTH: 31

```
<212> TYPE: PRT
<213> ORGANISM: Viola odorata
<220> FEATURE:
<223> OTHER INFORMATION: cycloviolacin 06

<400> SEQUENCE: 6

Cys Gly Glu Ser Cys Val Trp Ile Pro Cys Ile Ser Ala Ala Val Gly
1               5                   10                  15

Cys Ser Cys Lys Ser Lys Val Cys Tyr Lys Asn Gly Thr Leu Pro
            20                  25                  30

<210> SEQ ID NO 7
<211> LENGTH: 30
<212> TYPE: PRT
<213> ORGANISM: Viola odorata
<220> FEATURE:
<223> OTHER INFORMATION: cycloviolacin 07

<400> SEQUENCE: 7

Cys Gly Glu Ser Cys Val Trp Ile Pro Cys Thr Ile Thr Ala Leu Ala
1               5                   10                  15

Gly Cys Lys Cys Lys Ser Lys Val Cys Tyr Asn Ser Ile Pro
            20                  25                  30

<210> SEQ ID NO 8
<211> LENGTH: 30
<212> TYPE: PRT
<213> ORGANISM: Viola odorata
<220> FEATURE:
<223> OTHER INFORMATION: cycloviolacin 08

<400> SEQUENCE: 8

Cys Glu Ser Cys Val Trp Ile Pro Cys Ile Ser Ser Val Val Gly Cys
1               5                   10                  15

Ser Cys Lys Ser Lys Val Cys Tyr Lys Asn Gly Thr Leu Pro
            20                  25                  30

<210> SEQ ID NO 9
<211> LENGTH: 30
<212> TYPE: PRT
<213> ORGANISM: Viola odorata
<220> FEATURE:
<223> OTHER INFORMATION: cycloviolacin 09

<400> SEQUENCE: 9

Cys Gly Glu Ser Cys Val Trp Ile Pro Cys Leu Thr Ser Ala Val Gly
1               5                   10                  15

Cys Ser Cys Lys Ser Lys Val Cys Tyr Arg Asn Gly Ile Pro
            20                  25                  30

<210> SEQ ID NO 10
<211> LENGTH: 30
<212> TYPE: PRT
<213> ORGANISM: Viola odorata
<220> FEATURE:
<223> OTHER INFORMATION: cycloviolacin 10

<400> SEQUENCE: 10

Cys Gly Glu Ser Cys Val Tyr Ile Pro Cys Leu Thr Ser Ala Val Gly
1               5                   10                  15

Cys Ser Cys Lys Ser Lys Val Cys Tyr Arg Asn Gly Ile Pro
            20                  25                  30
```

```
<210> SEQ ID NO 11
<211> LENGTH: 31
<212> TYPE: PRT
<213> ORGANISM: Viola odorata
<220> FEATURE:
<223> OTHER INFORMATION: cycloviolacin 11

<400> SEQUENCE: 11

Cys Gly Glu Ser Cys Val Trp Ile Pro Cys Ile Ser Ala Val Val Gly
  1               5                  10                  15

Cys Ser Cys Lys Ser Lys Val Cys Tyr Lys Asn Gly Thr Leu Pro
             20                  25                  30

<210> SEQ ID NO 12
<211> LENGTH: 30
<212> TYPE: PRT
<213> ORGANISM: Viola odorata
<220> FEATURE:
<223> OTHER INFORMATION: cycloviolacin H1

<400> SEQUENCE: 12

Cys Gly Glu Ser Cys Val Tyr Ile Pro Cys Leu Thr Ser Ala Ile Gly
  1               5                  10                  15

Cys Ser Cys Lys Ser Lys Val Cys Tyr Arg Asn Gly Ile Pro
             20                  25                  30

<210> SEQ ID NO 13
<211> LENGTH: 30
<212> TYPE: PRT
<213> ORGANISM: Oldenlandia affinis
<220> FEATURE:
<223> OTHER INFORMATION: kalabata B5

<400> SEQUENCE: 13

Cys Gly Glu Ser Cys Val Tyr Ile Pro Cys Ile Ser Gly Val Ile Gly
  1               5                  10                  15

Cys Ser Cys Thr Asp Lys Val Cys Tyr Leu Asn Gly Thr Pro
             20                  25                  30

<210> SEQ ID NO 14
<211> LENGTH: 30
<212> TYPE: PRT
<213> ORGANISM: Chassalia parvifolia
<220> FEATURE:
<223> OTHER INFORMATION: circulin A

<400> SEQUENCE: 14

Cys Gly Glu Ser Cys Val Trp Ile Pro Cys Ile Ser Ala Ala Leu Gly
  1               5                  10                  15

Cys Ser Cys Lys Asn Lys Val Cys Tyr Arg Asn Gly Ile Pro
             20                  25                  30

<210> SEQ ID NO 15
<211> LENGTH: 31
<212> TYPE: PRT
<213> ORGANISM: Chassalia parvifolia
<220> FEATURE:
<223> OTHER INFORMATION: circulin B

<400> SEQUENCE: 15

Cys Gly Glu Ser Cys Val Phe Ile Pro Cys Ile Ser Thr Leu Leu Gly
  1               5                  10                  15
```

```
Cys Ser Cys Lys Asn Lys Val Cys Tyr Arg Asn Gly Val Ile Pro
            20                  25                  30
```

```
<210> SEQ ID NO 16
<211> LENGTH: 30
<212> TYPE: PRT
<213> ORGANISM: Psychotria longpipes
<220> FEATURE:
<223> OTHER INFORMATION: cyclopsychotride A

<400> SEQUENCE: 16
```

```
Cys Gly Glu Ser Cys Val Phe Ile Pro Cys Val Thr Ala Leu Leu Gly
 1               5                  10                  15

Cys Ser Cys Lys Ser Lys Val Cys Tyr Lys Asn Ser Ile Pro
            20                  25                  30
```

```
<210> SEQ ID NO 17
<211> LENGTH: 29
<212> TYPE: PRT
<213> ORGANISM: Artificial Sequence
<220> FEATURE:
<223> OTHER INFORMATION: violapeptide 1
<220> FEATURE:
<221> NAME/KEY: UNSURE
<222> LOCATION: 25
<223> OTHER INFORMATION: Any amino acid

<400> SEQUENCE: 17
```

```
Val Cys Gly Glu Thr Cys Val Gly Gly Thr Cys Asn Thr Pro Gly Cys
 1               5                  10                  15

Ser Cys Ser Arg Pro Val Cys Thr Xaa Asn Gly Leu Pro
            20                  25
```

```
<210> SEQ ID NO 18
<211> LENGTH: 29
<212> TYPE: PRT
<213> ORGANISM: Oldenlandia affinis
<220> FEATURE:
<223> OTHER INFORMATION: kalabata B1

<400> SEQUENCE: 18
```

```
Val Cys Gly Glu Thr Cys Val Gly Gly Thr Cys Asn Thr Pro Gly Cys
 1               5                  10                  15

Thr Cys Ser Trp Pro Val Cys Thr Arg Asn Gly Leu Pro
            20                  25
```

```
<210> SEQ ID NO 19
<211> LENGTH: 29
<212> TYPE: PRT
<213> ORGANISM: Oldenlandia affinis
<220> FEATURE:
<223> OTHER INFORMATION: kalabata B2

<400> SEQUENCE: 19
```

```
Val Cys Gly Glu Thr Cys Phe Gly Gly Thr Cys Asn Thr Pro Gly Cys
 1               5                  10                  15

Ser Cys Thr Trp Pro Ile Cys Thr Arg Asp Gly Leu Pro
            20                  25
```

```
<210> SEQ ID NO 20
<211> LENGTH: 30
<212> TYPE: PRT
<213> ORGANISM: Oldenlandia affinis
<220> FEATURE:
<223> OTHER INFORMATION: kalabata B3
```

```
<400> SEQUENCE: 20

Thr Cys Gly Glu Thr Cys Phe Gly Gly Thr Cys Asn Thr Pro Gly Cys
1               5                   10                  15

Thr Cys Asp Pro Trp Pro Ile Cys Thr Arg Asp Gly Leu Pro
            20                  25                  30

<210> SEQ ID NO 21
<211> LENGTH: 29
<212> TYPE: PRT
<213> ORGANISM: Oldenlandia affinis
<220> FEATURE:
<223> OTHER INFORMATION: kalabata B4

<400> SEQUENCE: 21

Val Cys Gly Glu Thr Cys Val Gly Gly Thr Cys Asn Thr Pro Gly Cys
1               5                   10                  15

Thr Cys Ser Trp Pro Val Cys Thr Arg Asp Gly Leu Pro
            20                  25

<210> SEQ ID NO 22
<211> LENGTH: 29
<212> TYPE: PRT
<213> ORGANISM: Viola arvensis
<220> FEATURE:
<223> OTHER INFORMATION: varv peptide A

<400> SEQUENCE: 22

Val Cys Gly Glu Thr Cys Val Gly Gly Thr Cys Asn Thr Pro Gly Cys
1               5                   10                  15

Ser Cys Ser Trp Pro Val Cys Thr Arg Asn Gly Leu Pro
            20                  25

<210> SEQ ID NO 23
<211> LENGTH: 30
<212> TYPE: PRT
<213> ORGANISM: Viola arvensis
<220> FEATURE:
<223> OTHER INFORMATION: varv peptide B

<400> SEQUENCE: 23

Val Cys Gly Glu Thr Cys Phe Gly Gly Thr Cys Asn Thr Pro Gly Cys
1               5                   10                  15

Ser Cys Asp Pro Trp Pro Met Cys Ser Arg Asn Gly Leu Pro
            20                  25                  30

<210> SEQ ID NO 24
<211> LENGTH: 29
<212> TYPE: PRT
<213> ORGANISM: Viola arvensis
<220> FEATURE:
<223> OTHER INFORMATION: varv peptide C

<400> SEQUENCE: 24

Ile Cys Gly Glu Thr Cys Val Gly Gly Thr Cys Asn Thr Pro Gly Cys
1               5                   10                  15

Ser Cys Ser Trp Pro Val Cys Thr Arg Asn Gly Val Pro
            20                  25

<210> SEQ ID NO 25
<211> LENGTH: 29
<212> TYPE: PRT
<213> ORGANISM: Viola arvensis
<220> FEATURE:
```

-continued

<223> OTHER INFORMATION: varv peptide D

<400> SEQUENCE: 25

Ile Cys Gly Glu Thr Cys Val Gly Gly Ser Cys Asn Thr Pro Gly Cys
1               5                   10                  15

Ser Cys Ser Trp Pro Val Cys Thr Arg Asn Gly Leu Pro
            20

```
<220> FEATURE:
<223> OTHER INFORMATION: native kalata B1

<400> SEQUENCE: 30

Cys Gly Glu Thr Cys Val Gly Gly Thr Cys Asn Thr Pro Gly Cys Thr
1               5                   10                  15

Cys Ser Trp Pro Val Cys Thr Arg Asn Gly Leu Pro Val
            20                  25

<210> SEQ ID NO 31
<211> LENGTH: 28
<212> TYPE: PRT
<213> ORGANISM: Artificial Sequence
<220> FEATURE:
<223> OTHER INFORMATION: synthetic peptide

<400> SEQUENCE: 31

Cys Gly Thr Cys Val Gly Gly Thr Cys Asn Thr Pro Gly Cys Thr Cys
1               5                   10                  15

Ser Trp Pro Val Cys Thr Arg Asn Gly Leu Pro Val
            20                  25

<210> SEQ ID NO 32
<211> LENGTH: 29
<212> TYPE: PRT
<213> ORGANISM: Artificial Sequence
<220> FEATURE:
<223> OTHER INFORMATION: synthetic peptide

<400> SEQUENCE: 32

Cys Gly Glu Thr Cys Val Gly Gly Thr Cys Asn Thr Pro Gly Cys Thr
1               5                   10                  15

Cys Ser Trp Pro Val Cys Thr Arg Asn Gly Leu Pro Val
            20                  25

<210> SEQ ID NO 33
<211> LENGTH: 27
<212> TYPE: PRT
<213> ORGANISM: Artificial Sequence
<220> FEATURE:
<223> OTHER INFORMATION: synthetic peptide

<400> SEQUENCE: 33

Cys Gly Glu Thr Cys Val Gly Gly Thr Cys Asn Gly Cys Thr Cys Ser
1               5                   10                  15

Trp Pro Val Cys Thr Arg Asn Gly Leu Pro Val
            20                  25

<210> SEQ ID NO 34
<211> LENGTH: 28
<212> TYPE: PRT
<213> ORGANISM: Artificial Sequence
<220> FEATURE:
<223> OTHER INFORMATION: synthetic peptide

<400> SEQUENCE: 34

Cys Gly Glu Thr Cys Val Gly Gly Thr Cys Asn Thr Pro Gly Cys Cys
1               5                   10                  15

Ser Trp Pro Val Cys Thr Arg Asn Gly Leu Pro Val
            20                  25

<210> SEQ ID NO 35
<211> LENGTH: 27
<212> TYPE: PRT
```

<213> ORGANISM: Artificial Sequence
<220> FEATURE:
<223> OTHER INFORMATION: synthetic peptide

<400> SEQUENCE: 35

Cys Gly Glu Thr Cys Val Gly Gly Thr Cys Asn Thr Pro Gly Cys Thr
1               5                   10                  15
Cys Ser Val Cys Thr Arg Asn Gly Leu Pro Val
            20                  25

<210> SEQ ID NO 36
<211> LENGTH: 24
<212> TYPE: PRT
<213> ORGANISM: Artificial Sequence
<220> FEATURE:
<223> OTHER INFORMATION: synthetic peptide

<400> SEQUENCE: 36

Cys Gly Glu Thr Cys Val Gly Gly Thr Cys Asn Thr Pro Gly Cys Thr
1               5                   10                  15
Cys Ser Trp Pro Val Cys Thr Val
            20

<210> SEQ ID NO 37
<211> LENGTH: 29
<212> TYPE: PRT
<213> ORGANISM: Artificial Sequence
<220> FEATURE:
<223> OTHER INFORMATION: synthetic peptide

<400> SEQUENCE: 37

Cys Gly Glu Thr Cys Val Gly Gly Thr Cys Asn Thr Pro Gly Cys Thr
1               5                   10                  15
Cys Ser Trp Pro Val Cys Thr Arg Asn Gly Leu Pro Val
            20                  25

<210> SEQ ID NO 38
<211> LENGTH: 31
<212> TYPE: PRT
<213> ORGANISM: Artificial Sequence
<220> FEATURE:
<223> OTHER INFORMATION: Synthetic peptide

<400> SEQUENCE: 38

Cys Thr Cys Arg Ser Gly Lys Cys Thr Arg Asn Gly Leu Pro Val Cys
1               5                   10                  15
Gly Glu Thr Cys Ser Arg Leu Met Tyr Asp Cys Asn Thr Pro Gly
            20                  25                  30

<210> SEQ ID NO 39
<211> LENGTH: 29
<212> TYPE: PRT
<213> ORGANISM: Artificial Sequence
<220> FEATURE:
<223> OTHER INFORMATION: Synthetic peptide

<400> SEQUENCE: 39

Cys Thr Cys Arg Gly Asp Val Cys Thr Arg Asn Gly Leu Pro Val Cys
1               5                   10                  15
Gly Glu Thr Cys Val Gly Gly Thr Cys Asn Thr Pro Gly
            20                  25

<210> SEQ ID NO 40
<211> LENGTH: 32

```
<212> TYPE: PRT
<213> ORGANISM: Artificial Sequence
<220> FEATURE:
<223> OTHER INFORMATION: Synthetic peptide

<400> SEQUENCE: 40

Cys Thr Cys Ser Trp Pro Val Cys Thr Arg Asn Gly Leu Pro Val Cys
1               5                   10                  15

Pro Lys Ile Leu Lys Lys Cys Val Gly Gly Thr Cys Asn Thr Pro Gly
            20                  25                  30

<210> SEQ ID NO 41
<211> LENGTH: 34
<212> TYPE: PRT
<213> ORGANISM: Artificial Sequence
<220> FEATURE:
<223> OTHER INFORMATION: Synthetic peptide

<400> SEQUENCE: 41

Cys Ile Cys Arg Gly Asn Gly Tyr Cys Gly Ser Gly Ser Asp Gly Gly
1               5                   10                  15

Val Cys Lys Lys Arg Ser Trp Pro Cys Arg Arg Asp Ser Asp Cys Pro
            20                  25                  30

Gly Ala

<210> SEQ ID NO 42
<211> LENGTH: 29
<212> TYPE: PRT
<213> ORGANISM: Artificial Sequence
<220> FEATURE:
<223> OTHER INFORMATION: Synthetic peptide

<400> SEQUENCE: 42

Cys Thr Cys His Phe Arg Trp Cys Thr Arg Asn Gly Leu Pro Val Cys
1               5                   10                  15

Gly Glu Thr Cys Val Gly Gly Thr Cys Asn Thr Pro Gly
            20                  25

<210> SEQ ID NO 43
<211> LENGTH: 30
<212> TYPE: PRT
<213> ORGANISM: Artificial Sequence
<220> FEATURE:
<223> OTHER INFORMATION: Synthetic peptide

<400> SEQUENCE: 43

Cys Thr Cys His Phe Arg Trp Asn Cys Thr Arg Asn Gly Leu Pro Val
1               5                   10                  15

Cys Gly Glu Thr Cys Val Gly Gly Thr Cys Asn Thr Pro Gly
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: UNSURE
<222> LOCATION: 4
<223> OTHER INFORMATION: N-methyl phenylalanine
<220> FEATURE:
<221> NAME/KEY: UNSURE
<222> LOCATION: 5
<223> OTHER INFORMATION: Ornithine
<220> FEATURE:
```

```
<221> NAME/KEY: UNSURE
<222> LOCATION: 7
<223> OTHER INFORMATION: Cyclohexyalanine

<400> SEQUENCE: 44

Cys Thr Cys Xaa Xaa Pro Xaa Trp Arg Cys Thr Arg Asn Gly Leu Pro
1               5                   10                  15

Val Cys Gly Glu Thr Cys Val Gly Gly Thr Cys Asn Thr Pro Gly
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: UNSURE
<222> LOCATION: 25
<223> OTHER INFORMATION: N-methyl phenyalanine
<220> FEATURE:
<221> NAME/KEY: UNSURE
<222> LOCATION: 26
<223> OTHER INFORMATION: Ornithine
<220> FEATURE:
<221> NAME/KEY: UNSURE
<222> LOCATION: 28
<223> OTHER INFORMATION: Cyclohexyalanine

<400> SEQUENCE: 45

Cys Ser Cys Lys Asn Lys Val Cys Tyr Arg Asn Gly Ile Pro Cys Gly
1               5                   10                  15

Glu Ser Cys Val Trp Ile Pro Cys Xaa Xaa Pro Xaa Trp Arg
            20                  25                  30

<210> SEQ ID NO 46
<211> LENGTH: 34
<212> TYPE: PRT
<213> ORGANISM: Momordica cochinchinensis
<220> FEATURE:
<223> OTHER INFORMATION: McoTI-I

<400> SEQUENCE: 46

Val Cys Pro Lys Ile Leu Gln Arg Cys Arg Arg Asp Ser Asp Cys Pro
1               5                   10                  15

Gly Ala Cys Ile Cys Arg Gly Asn Gly Tyr Cys Gly Ser Gly Ser Asp
            20                  25                  30

Gly Gly

<210> SEQ ID NO 47
<211> LENGTH: 34
<212> TYPE: PRT
<213> ORGANISM: Momordica cochinchinensis
<220> FEATURE:
<223> OTHER INFORMATION: McoTI-II

<400> SEQUENCE: 47

Val Cys Pro Lys Ile Leu Lys Lys Cys Arg Arg Asp Ser Asp Cys Pro
1               5                   10                  15

Gly Ala Cys Ile Cys Arg Gly Asn Gly Tyr Cys Gly Ser Gly Ser Asp
            20                  25                  30

Gly Gly
```

CYCLIC MOLECULAR FRAMEWORK AND DERIVATIVES THEREOF

This application is a continuation of U.S. application Ser. No. 10/121,282 filed Apr. 12, 2002, now abandoned, which is a continuation of International Patent Application No. PCT/AU00/01248, now International Publication No. WO 01/27147, published in English on Apr. 19, 2001, and filed on Oct. 13, 2000, which claimed priority to Australian Patent Application No. PQ3398, filed Oct. 13, 1999, each of which are incorporated by reference in their entireties herein, and from which priority is claimed and is incorporated by reference.

FIELD OF THE INVENTION

The present invention relates generally to a molecular framework having a cyclic structure. More particularly, the present invention provides cyclic proteins and derivatives thereof in which particular turns and other elements of the molecular structure are held in defined orientations with respect to each other. The cyclic proteins of the present invention provide a molecular framework for the introduction of particular amino acids or heterologous amino acid sequences to facilitate the presentation of biological activities associated with these heterologous amino acid sequences. The molecular framework of the present invention may be naturally cyclic or may be a cyclized derivative of a linear molecule or may be a linear derivative of a cyclized molecule. The present invention contemplates the use of the molecular framework with or without particular amino acids inserted or substituted thereon for the treatment of prophylaxis of disease conditions in animals, mammals (including human) and plants.

BACKGROUND OF THE INVENTION

Reference to any prior art in this specification is not, and should not be taken as, an acknowledgment or any form of suggestion that this prior art forms part of the common general knowledge in Australia or any other country.

Bibliographic details of the publications referred to by author in this specification are collected at the end of the description.

Proteins have been traditionally regarded as linear chains of amino acids which fold into a defined three-dimensional shape necessary to enable their biological function. In many proteins, the linear peptide backbone is cross-linked via disulfide bonds between cysteine residues but even in these cases, the three dimensional folds are generally topologically simple and are not knotted.

Certain plants of the Rubiaceae and Violaceae families provide small cyclic proteins in the order of approximately 30 amino acids. The cyclization involves an amide bond resulting in no identifiable N- or C-terminus in the molecule. Notable examples of these small cyclic molecules are the circulins (Gustafson et al, 1994), kalata B1 (Saether et al, 1995), cyclopsychotride (Witherup et al, 1994) and several molecules from the Violaceae family (Schopke et al, 1993; Claeson et al, 1998; Goransson et al, 1999).

These small cyclic proteins have diverse activities including anti-microbial properties, haemolytic activities and as uterotonic agents. However, the biological function of cyclic proteins in plants is largely unknown.

In work leading up to the present invention, the inventors have characterized a new family of cyclic proteins. The cyclic proteins exhibit conserved cysteine residues defining a structure referred to herein as a "cystine knot". This family includes both naturally occurring cyclic molecules and their linear derivatives as well as linear molecules which have undergone cyclization. These molecules are useful as molecular framework structures having enhanced stability over their linear counterparts.

SUMMARY OF THE INVENTION

One aspect of the present invention contemplates a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

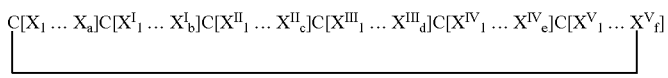

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and each of a to f may be the same or different and range from 1 to about 20;

or an analogue of said sequence.

Another aspect of the present invention contemplates a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

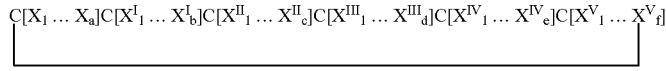

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and each of a to f may be the same or different and range from 1 to about 10;

or an analogue of said sequence.

A further aspect of the present invention provides a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

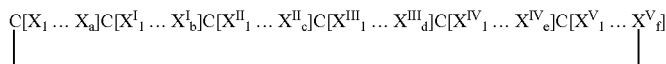

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and wherein a is from about 3 to about 6, b is from about 3 to about 5, c is from about 2 to about 7, d is about 1 to about 3, e is about 3 to about 6 and f is from about 4 to about 9;

or an analogue of said sequence.

Yet a further aspect of the present invention provides a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

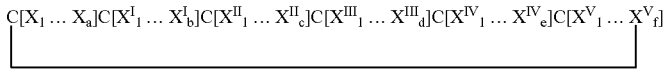

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and wherein a is about 3, b is about 4, c is from about 4 to about 7, d is about 1, e is about 4 or 5 and f is from about 4 to about 7;

or an analogue of said sequence.

Still a further aspect of the present invention provides a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

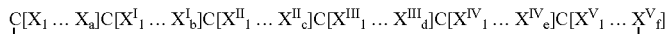

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and wherein a is about 6, b is about 5, c is about 3, d is about 1, e is about 5 and f is about 8;

or an analogue of said sequence.

Yet another aspect of the present invention is directed to a molecular framework comprising a sequence of amino acids or analogues thereof forming a cyclic backbone and wherein said cyclic backbone comprises sufficient disulfide bonds or chemical equivalents thereof, to confer a knotted topology on the three-dimensional structure of said cyclic backbone and wherein at least one exposed amino acid residue such as on one or more beta turns and/or within one or more loops, is inserted or substituted relative to the naturally occurring amino acid sequence.

Even yet another aspect of the present invention contemplates a molecular framework comprising a sequence of amino acids or analogues thereof forming a cyclic backbone and wherein said cyclic backbone comprises a cystine knot or its chemical or structural equivalent which confers a knotted topology on the three-dimensional structure of said cyclic backbone and wherein at least one exposed amino acid residue such as on one or more beta turns and/or within one or more loops is inserted or substituted relative to the naturally occurring amino acid sequence.

Another aspect of the present invention is directed to a molecular framework comprising a sequence of amino acids or analogues thereof forming a cyclic cystine knot motif defined by a cyclic backbone, at least three disulfide bonds and associated beta strands in a defined knotted topology and wherein at least one exposed amino acid residue such as on one or more beta turns or within one or more loops is inserted or substituted relative to the naturally occurring amino acid sequence.

A further aspect of the present invention is directed to antibodies to the molecular framework of the present invention.

Still a further aspect of the present invention provides a method for the treatment or prophylaxis of conditions or diseases in mammals, preferably humans, including the step of administering a molecular framework as hereinbefore described either without modification or having heterologous amino acids grafted thereon.

Yet another aspect of the present invention provides a composition comprising cyclic molecular framework molecules as hereinbefore described and a pharmaceutically acceptable carrier and/or diluent.

Even yet another aspect of the present invention provides a method for conferring pathogen protection to a plant, including the step of administering an engineered framework as hereinbefore described.

A plant pathogen includes a spider, insect, fungus, virus and bacterium.

Another aspect of the present invention contemplates a method for detecting a molecular framework as described herein in a sample, said method comprising contacting said sample with an antibody or other immunointeractive molecule specific for said molecular framework or its derivatives or homologues for a time and under conditions sufficient for an antibody-molecular framework complex to form, and then detecting said complex.

Single and three letter abbreviations used throughout the specification are defined in Table

TABLE 1

Single and three letter amino acid abbreviations

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |

TABLE 1-continued

Single and three letter amino acid abbreviations

| Amino Acid | Three-letter Abbreviation | One-letter Symbol |
|---|---|---|
| Valine | Val | V |
| Any residue | Xaa | X |

BRIEF DESCRIPTION OF THE FIGURES

FIG. 3 is a diagrammatic representation showing topologies of cystine knot peptides. (a) The common cysteine connectivity of known cystine knot peptides from plants, animals and fungi. This connectivity pattern can be redrawn to illustrate that the pattern is topologically simple, i.e. involves no line crossings in two dimensions, as shown in (b). Circularization of the backbone, as in (c), removes this topological simplicity, as occurs in the CCK family of cyclotides. Other non-knotted arrangements of disulfide connectivities are, however, theoretically feasible, as shown in (d). The series (e) to (h) shows successive unfolding of non-cyclic cystine knot peptides, demonstrating their topological simplicity. This unfolding is based on a kinemage from Benham and Jafri (1993).

Figure 1:
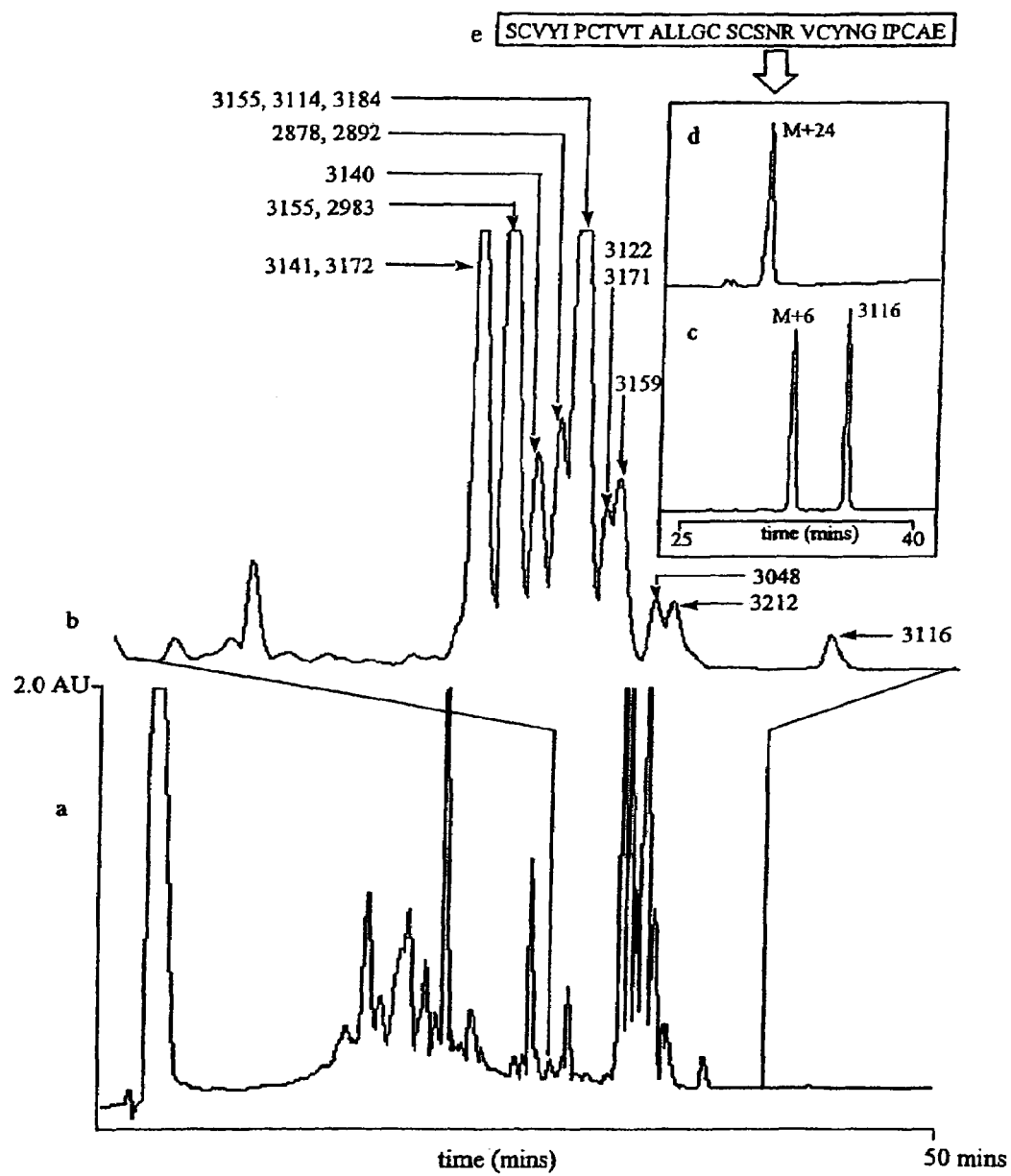
FIG. 1 is a diagrammatic representation of the isolation and characterization of cycloviolacin 01; (a) HPLC profile of the crude extract from *V. odorata*. The region of interest is expanded in (b) to show the peptide peaks labelled with their mass. Cycloviolacin 01 eluted last in this profile. The peptide was reduced with tris-carboxyethylphosphine (TCEP) and alkylated with maleimide. (c) The reduced and alkylated species (labelled M+6), which has a mass 582 Da greater than the native peptide since 97 Da was added to each of the six cysteine residues during alkylation, was purified under the same HPLC conditions and eluted five mins earlier than the native peptide. The reduced and alkylated species was cleaved with Endoproteinase Glu-C to facilitate sequencing. (d) The cleaved species (labelled M+24), has a mass 18 Da greater than the reduced and alkylated peptide due to addition of $H_2O$ across the cleaved peptide bound. (e) N-terminal sequencing of cycloviolacin 01 for 30 cycles yielded the indicated sequence.

Table 2 is a summary of amino acid and nucleotide sequence identifiers.

TABLE 2

| SEQUENCE IDENTIFIER | DESCRIPTION |
|---|---|
| SEQ ID NO:1 | cycloviolacin 01 |
| SEQ ID NO:2 | cycloviolacin 02 |
| SEQ ID NO:3 | cycloviolacin 03 |
| SEQ ID NO:4 | cycloviolacin 04 |
| SEQ ID NO:5 | cycloviolacin 05 |
| SEQ ID NO:6 | cycloviolacin 06 |
| SEQ ID NO:7 | cycloviolacin 07 |
| SEQ ID NO:8 | cycloviolacin 08 |
| SEQ ID NO:9 | cycloviolacin 09 |
| SEQ ID NO:10 | cycloviolacin 010 |
| SEQ ID NO:11 | cycloviolacin 011 |
| SEQ ID NO:12 | cycloviolacin H1 |
| SEQ ID NO:13 | kalata B5 |
| SEQ ID NO:14 | circulin A |
| SEQ ID NO:15 | circulin B |
| SEQ ID NO:16 | cyclopsychotride A |
| SEQ ID NO:17 | violapeptide 1 |
| SEQ ID NO:18 | kalata B1 |
| SEQ ID NO:19 | kalata B2 |
| SEQ ID NO:20 | kalata B3 |
| SEQ ID NO:21 | kalata B4 |
| SEQ ID NO:22 | varv peptide A |
| SEQ ID NO:23 | varv peptide B |
| SEQ ID NO:24 | varv peptide C |
| SEQ ID NO:25 | varv peptide D |
| SEQ ID NO:26 | varv peptide E |
| SEQ ID NO:27 | varv peptide F |
| SEQ ID NO:28 | varv peptide G |
| SEQ ID NO:29 | varv peptide H |
| SEQ ID NO:30 | native kalata B1 |
| SEQ ID NO:31 | des-(3)-kalata B1 |
| SEQ ID NO:32 | kalata B1-(8-7) |
| SEQ ID NO:33 | des(12-13)-kalata B1 |
| SEQ ID NO:34 | des(16)-kalata B1 |
| SEQ ID NO:35 | des(19-20)-kalata B1 |
| SEQ ID NO:36 | des(24-28)-kalata B1 |
| SEQ ID NO:37 | kalata B1-(24-23) |
| SEQ ID NO:38 | synthetic peptide |
| SEQ ID NO:39 | synthetic peptide |
| SEQ ID NO:40 | synthetic peptide |
| SEQ ID NO:41 | synthetic peptide |

TABLE 2-continued

| SEQUENCE IDENTIFIER | DESCRIPTION |
|---|---|
| SEQ ID NO:42 | synthetic peptide |
| SEQ ID NO:43 | synthetic peptide |
| SEQ ID NO:44 | synthetic peptide |
| SEQ ID NO:45 | synthetic peptide |
| SEQ ID NO:46 | Mco-TI-I |
| SEQ ID NO:47 | McoTI-II |

DETAILED DESCRIPTION OF THE PREFERRED EMBODIMENTS

The present invention provides a molecular framework comprising a sequence of amino acids or analogues thereof forming a cyclic backbone and wherein said cyclic backbone comprises sufficient disulfide bonds, or chemical equivalents thereof, to confer a knotted topology on the three-dimensional structure of said cyclic backbone.

Reference herein to a "molecular framework" includes a proteinaceous molecule having a defined three-dimensional structure. This defined three-dimensional structure comprises loops of amino acid residues and other elements of molecular structure held in defined orientation with respect to each other. The molecular framework itself may exhibit a particularly useful property such as having anti-pathogen activities such as against viruses, microorganisms, fungi, yeast, arachnids and insects or it may confer useful therapeutic properties in plants or animals. Furthermore, it may provide the framework for inserting one or more amino acids or amino acid sequences capable of conferring a desired biological effect. Insertion of the one or more amino acid residues or sequences may occur on a β-turn or within a loop. The molecular framework may also be presented in a linear form as a substrate for cyclization. Alternatively, a cyclic molecule may be derivatized into linear form which itself may have useful properties or it may act as an agonist or antagonist of such properties.

The sequence of amino acids forming the backbone of the molecular framework may be naturally occurring amino acid residues or chemical analogues thereof. Chemical analogues of amino acid residues include non-naturally occurring amino acids. Examples of non-naturally occurring amino acids are shown in Table 3.

By way of example, when a molecular framework in the form of a cyclic polypeptide is isolated and purified from a biological source, such as a plant, the molecule generally comprises naturally occurring amino acid residues. However, the present invention extends to derivatives of such a molecular framework by inserting or substituting non-naturally occurring amino acid residues or chemical analogues of amino acid residues. Alternatively, single and/or a heterologous sequence of naturally occurring amino acid residues may be inserted or substituted into the molecular framework to confer desired properties on the molecule.

Reference herein to a "cyclic backbone" includes a molecule comprising a sequence of amino acid residues or analogues thereof without free amino and carboxy termini.

Preferably, the linkage between all amino acids in the cyclic backbone is via amide (peptide) bonds, but other chemical linkers are also possible.

The cyclic backbone of the molecular framework of the present invention comprises sufficient disulfide bonds, or chemical equivalents thereof, to confer a knotted topology on the three-dimensional structure of the cyclic backbone.

In a preferred embodiment, the cyclic backbone comprises a structure referred to herein as a "cystine knot". A cystine knot occurs when a disulfide bond passes through a closed cyclic loop formed by two other disulfide bonds and the amino acids in the backbone. Such a cystine knot is referred to herein as a "cyclic cystine knot" or "CCK". However, reference herein to a "cyclic cystine knot" or a "CCK" includes reference to structural equivalents thereof which provide similar constraints to the three-dimensional structure of the cyclic backbone. For example, appropriate turns and loops in the cyclic backbone may also be achieved by engineering suitable covalent bonds or other forms of molecular associations. All such modifications to the cyclic backbone which result in retention of the three-dimensional knotted topology conferred by the cyclic cystine knot are encompassed by the present invention. Furthermore, although a cyclic cystine knot is characterized by a knot formed by three disulfide bonds, the present invention extends to molecules comprising only two disulfide bonds. In such a case, the molecular framework may need to be further stabilized using other means or the molecular framework may retain suitable activity despite a change in three-dimensional structure caused by the absence of a third disulfide bond.

In yet a further modification, the cyclic backbone may comprise more than three disulfide bonds such as occurring in a double or multiple cystine knot arrangement or in a single cystine knot arrangement supplement by one or two additional disulfide bonds.

All such modifications are still encompassed by the term "cyclic cystine knot" or "CCK".

The terms "knot" and "cystine knot" are not to be limited by any mathematical or geometrical definition of the term "knot". The knots contemplated by the present invention are such due to their similarity to a mathematical knot and/or by virtue of the intertwined folding of the molecule which results.

The present invention provides, therefore, a molecular framework comprising a sequence of amino acids or analogues thereof forming a cyclic backbone and wherein said cyclic backbone comprises a cystine knot or its chemical or structural equivalent which confers a knotted topology on the three-dimensional structure of said cyclic backbone.

Accordingly, one aspect of the present invention contemplates a molecular framework comprising a sequence of amino acids forming a cyclic backbone wherein the cyclic backbone comprises sufficient disulfide bonds or chemical equivalents hereof to confer knotted topology on the molecular framework or part thereof wherein said cyclic backbone comprises the structure:—

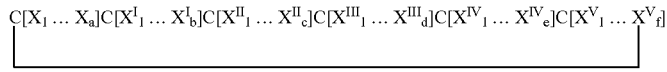

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and each of a to f may be the same or different and range from 1 to about 20;

or an analogue of said sequence.

Preferably, each of a to f ranges from 1 to about 10.

In still an even more particularly preferred embodiment, the present invention provides a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

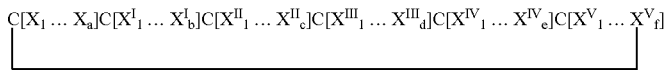

wherein

C is cysteine;

each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and wherein a, b, c, d, e and f represent the number of amino acid residues in each respective sequence and wherein a is from about 3 to about 6, b is from about 3 to about 5, c is from about 2 to about 7, d is about 1 to about 3, e is about 3 to about 6 and f is from about 4 to about 9;

or an analogue of said sequence.

In yet an even more particularly preferred embodiment, the present invention provides a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

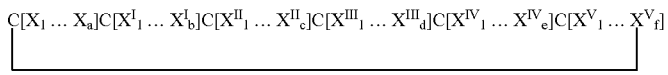

wherein
C is cysteine;
each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
wherein a, b, c, d, e and f represent the number of amino acid residues in each respective sequence and wherein a is about 3, b is about 4, c is from about 4 to about 7, d is about 1, e is about 4 or 5 and f is from about 4 to about 7;
or an analogue of said sequence.

In a further preferred embodiment, the present invention provides a molecular framework comprising a sequence of amino acids forming a cyclic backbone wherein the cyclic backbone comprises sufficient disulfide bonds or chemical equivalents thereof to confer knotted topology on the molecular framework or part thereof wherein said cyclic backbone comprises the structure:—

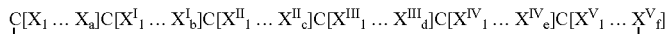

wherein
C is cysteine;
each of $[X_1 \ldots X_a]$, $[X^I_1 \ldots X^I_b]$, $[X^{II}_1 \ldots X^{II}_c]$, $[X^{III}_1 \ldots X^{III}_d]$, $[X^{IV}_1 \ldots X^{IV}_e]$ and $[X^V_1 \ldots X^V_f]$ represents one or more amino acid residues wherein each one or more amino acid residues within or between the sequence residues may be the same or different; and
wherein a, b, c, d, e and f represent the number of amino acid residues in each respective sequence and wherein a is about 6 b is about 5, c is about 3, d is about 1, e is about 5 and f is about 8;
or an analogue of said sequence.

The molecular framework of the present invention has particular advantages in relation to one or more of increased chemical stability, resistance to protease cleavage and improved bioavailability.

The molecular framework of the present invention is also referred to herein as a "cyclotide". A cyclotide is regarded as being equivalent to a molecular framework as herein described and, in its most preferred embodiment, comprises a cyclic cystine knot motif defined by a cyclic backbone, at least two but preferably at least three disulfide bonds and associated beta strands in a particular knotted topology. The knotted topology involves an embedded ring formed by at least two backbone disulfide bonds and their connecting backbone segments being threaded by a third disulfide bond. As stated above, however, a disulfide bond may be replaced or substituted by another form of bonding such as a covalent bond.

The molecular framework of the present invention permits modifications to be made to the molecule while retaining the stable structural scaffold. Such modifications include, for example, different amino acid residues inserted or substituted anywhere in the molecule but preferably in one or more beta-turns and/or within a loop. The newly exposed amino acids, for example, may provide functional epitopes or activities not present in the molecular framework prior to modification. Alternatively, the newly exposed amino acids may enhance an activity already possessed by the molecular framework. A substitution or insertion may occur at a single location or at multiple locations. Furthermore, the molecular framework may be specifically selected to more readily facilitate substitution and/or insertion of amino acid sequences. Such modified forms of the molecular framework are proposed to have a range of useful properties including as therapeutic agents for animals and mammals (including humans) and plants. Therapeutic agents for plants include pest control agents. As stated above, the molecular framework has advantages in terms of increased stability relative to, for example, conventional peptide drugs. The increased stability includes resistance or less susceptibility to protease cleavage. Furthermore, the molecules may have a hydrophobic face which may benefit their interaction with membranes while still being highly water soluble. This may improve their bioavailability.

Accordingly, another aspect of the present invention is directed to a molecular framework comprising a sequence of amino acids or analogues thereof forming a cyclic backbone and wherein said cyclic backbone comprises sufficient disulfide bonds or chemical equivalents thereof, to confer a knotted topology on the three-dimensional structure of said cyclic backbone and wherein at least one exposed amino acid residue such as on one or more beta turns and/or within one or more loops, is inserted or substituted relative to the naturally occurring amino acid sequence.

Even more particularly, the present invention contemplates a molecular framework comprising a sequence of amino acids or analogues thereof forming a cyclic backbone and wherein said cyclic backbone comprises a cystine knot or its chemical or structural equivalent which confers a knotted topology on the three-dimensional structure of said cyclic backbone and wherein at least one exposed amino acid residue such as on one or more beta turns and/or within one or more loops is inserted or substituted relative to the naturally occurring amino acid sequence.

More particularly, the present invention is directed to a molecular framework comprising a sequence of amino acids or analogues thereof forming a cyclic cystine knot motif defined by a cyclic backbone, at least three disulfide bonds and associated beta stands in a defined knotted topology and wherein at least one exposed amino acid residue such as on one or more beta turns or within one or more loops is inserted or substituted relative to the naturally occurring amino acid sequence.

Although the inserted or substituted amino acid is preferably an exposed amino acid on a beta turn, the present invention contemplates an inserted or substituted amino acid anywhere on the molecule.

The inserted or substituted amino acid residues may be a single residue or may be a linear sequence of from about two residues to about 60 residues, preferably from about two to about 30 residues, and even more preferably, from about 2 residues to about 10 residues. The insertion or substitution may occur at a single location or at multiple locations. The latter includes the insertion of non-contiguous amino acid sequences. Furthermore, different amino acid molecules may be inserted/substituted at different sites on the molecule. This is particularly useful in the preparation of multivalent or multifunctional molecules.

These inserted or substituted residues are referred to as being heterologous relative to the amino acid sequence naturally occurring in the molecular framework. The term "graft" or its various derivations is used in the specification to refer to amino acid insertions and/or substitutions.

The heterologous amino acids inserted or substituted in the molecular framework have the capacity to confer a range of activities and biological properties to the molecule including modulating calcium channel-binding, which is useful in the treatment of pain or a stroke, C5a binding, useful as an anti-inflammatory agent, proteinase inhibitor activity in plants or animals, antibiotic activity, HIV activity, microbial activity, fungal activity, viral activity, cytokine binding ability and blood clot inhibition and plant pathogen activity (e.g. insecticidal activity) amongst other properties. The molecule may be a modulator in the sense that it may facilitate the activity or inhibit the activity. Accordingly, the molecule may act as an agonist or antagonist. Furthermore, the heterologous amino acids may form a sequence which may be readily cleaved to form an open-ended circle or which is required to be activated by proteinase cleavage.

The present invention encompasses a range of amino acid substitutions, additions and/or insertions to the amino acid sequence of the molecular framework.

Substitutions encompass amino acid alterations in which an amino acid is replaced with a different naturally-occurring or a non-conventional amino acid residue. Such substitutions may be classified as "conservative", in which case an amino acid residue contained in a polypeptide is replaced with another naturally-occurring amino acid of similar character either in relation to polarity, side chain functionality, or size, for example, Ser↔Thr↔Pro↔Hyp↔Gly↔Ala, Val↔Ile↔Leu, His↔Lys↔Arg, Asn↔Gln↔Asp↔Glu or Phe↔Trp↔Tyr. It is to be understood that some non-conventional amino acids may also be suitable replacements for the naturally occurring amino acids. For example, ornithine, homoarginine and dimethyllysine are related to His, Arg and Lys.

Substitutions encompassed by the present invention may also be "non-conservative", in which an amino acid residue which is present in a polypeptide is substituted with an amino acid having different properties, such as a naturally-occurring amino acid from a different group (e.g. substituting a charged or hydrophobic amino acid with alanine), or alternatively, in which a naturally-occurring amino acid is substituted with a non-conventional amino acid.

Amino acid substitutions are typically of single residues, but may be of multiple residues, either clustered or dispersed.

Amino acids of the cyclic peptide backbone are preferably conservative in order to maintain the three-dimensional structure in a form functionally similar to the cyclic peptide before derivatization. Substitutions of amino acid residues in the cyclic peptide to introduce or otherwise graft heterologous sequences onto the backbone need not be conservative.

Additions encompass the addition of one or more naturally occurring or non-conventional amino acid residues. Deletion encompasses the deletion of one or more amino acid residues.

The present invention also includes molecules in which one or more of the amino acids has undergone side chain modifications. Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitization, for example, to a corresponding amide.

Sulphydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl groups of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residues may be modified by, for example, hydroxylation in the 4-position.

Other modifications include succinimide derivatives of aspartic acid.

A list of some amino acids having modified side chains and other unnatural amino acids is shown in Table 3.

TABLE 3

| Non-conventional amino acid | Code | Non-conventional amino acid | Code |
|---|---|---|---|
| α-aminobutyric acid | Abu | L-N-methylalanine | Nmala |
| α-amino-α-methyl-butyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| α-aspartic acid | Aaa |  |  |
| β-aspartic acid | Baa |  |  |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenyl-alanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |

TABLE 3-continued

| Non-conventional amino acid | Code | Non-conventional amino acid | Code |
|---|---|---|---|
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methyl-butyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methyhnethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl)carbamylmethyl)glycine | Nnbhm | N-(N-(3,3-diphenylpropyl)carbamylmethyl)glycine | Nnbhe |
| 1-carboxy-1-(2,2-diphenylethylamino)cyclopropane | Nmbc | | |

These types of modifications may be important to further stabilise the molecular framework especially if administered to a subject or used as a diagnostic reagent or in agricultural applications (e.g. topical sprays).

Other derivatives contemplated by the present invention include a range of glycosylation variants from a completely unglycosylated molecule to a modified glycosylated molecule. Altered glycosylation patterns may result from expression of recombinant molecules in different host cells.

The present invention flier contemplates linear molecules of from about 20 amino acids to about 100 amino acids and more preferably from about 25 amino acids to about 50 amino acids such as about 30 amino acids which are used as substrates for cyclization reactions. The resulting cyclized molecules having the same or functionally similar structure as the cyclic framework as herein described.

As stated above, the present invention extends to a range of derivatives, homologues and analogues of the molecular framework. A derivative includes parts, fragments, portions and linear forms. One particularly useful linear form is preferred to herein as "uncycles" which are acyclic permutations of the cyclic molecular framework. Circular permutation involves the synthesis or expression of proteins having amino and carboxy termini permuted from their native locality. In relation to the naturally occurring cyclic molecular frameworks of the present invention, such molecules do not have native amino and carboxy termini. However, cyclic permutation permits a range of different linear molecules to be prepared with different amino and carboxy termini. An uncycle may have increased activity relative to its cyclic form or no activity or may exhibit antagonist activity. An uncycle exhibiting no activity may nevertheless be useful, for example, in the generation of antibodies.

By way of example only, particularly preferred CCK molecules comprise six cysteine residues and, hence, have six loops in the backbone which can be opened to form six possible topologically distinct acyclic permutants. Similarly, each of the 6 linear topologies may also be cyclized. This aspect of the present invention provides, therefore, to the cyclization of any linear topology into a CCK framework.

The uncycles of the present invention may be useful as antagonists of the cyclic molecular framework or may themselves exhibit useful activity.

Still another aspect of the present invention is directed to antibodies to the molecular framework of the present invention. Such antibodies may be monoclonal or polyclonal. Polyclonal antibodies are particularly preferred. Antibodies may be made using standard techniques.

The preparation of hybridoma cell lines for monoclonal antibody production derived by fusing an immortal cell line and lymphocytes sensitized against an immunogenic preparation comprising a molecular framework can be done by techniques which are well known to those who are skilled in the art. (See, for example, Douillard and Hoffman, 1981; Kohler and Milstein, 1975 and 1976.)

The antibodies of the present invention are particularly useful as therapeutic or diagnostic agents or as a means for purifying a molecular framework from a biological sample.

In this regard, specific antibodies can be used to screen for the molecular framework according to the present invention. Techniques for such assays are well known in the art and include, for example, sandwich assays and ELISA. Knowledge of molecular framework levels may be important for monitoring certain therapeutic protocols.

Another aspect of the present invention contemplates a method for detecting a molecular framework as described herein in a sample, said method comprising contacting said sample with an antibody or other immunointeractive molecule specific for said molecular framework or its derivatives or homologues for a time and under conditions sufficient for an antibody-molecular framework complex to form, and then detecting said complex.

The presence of a molecular framework may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, includes both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of antigen. Variations on the forward assay include a simultaneous assay, in which both sample and labelled antibody are added simultaneously to the bound antibody. These techniques are well known to those skilled in the art, including any minor variations as will be readily apparent. In accordance with the present invention, the sample is one which might contain a molecular framework including cell extract, tissue biopsy or possibly serum, saliva, mucosal secretions, lymph, tissue fluid and respiratory fluid. The sample is, therefore, generally a biological sample comprising biological fluid but also extends to fermentation fluid, supernatant fluid such as from a cell culture as well as a sample arising from a chemical synthesis.

In a typical forward sandwich assay, a first antibody having specificity for the molecular framework or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 240 minutes or overnight if more convenient) and under suitable conditions (e.g. from room temperature to about 37° C. including 25° C.) to allow binding of the antibody. Following the incubation period, the solid phase is washed and dried and incubated with a second antibody specific for a portion of the antigen. The second antibody is linked to a reporter molecule which is used to indicate the binding of the second antibody to the hapten.

An alternative method involves immobilizing the target molecules in the sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule", as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme imunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody.

The substrate will react with the enzyme linked to the second antibody, giving a qualitative visual signal, which may be further quantitated, usually spectrophotometrically, to give an indication of the amount of hapten which was present in the sample. "reporter molecule" also extends to use of cell agglutination or inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength, the fluorescence observed indicates the presence of the hapten of interest. Immunofluorescene and EIA techniques are both very well established in the art and are particularly preferred for the present method. However, other reporter molecules, such as radioisotope, chemiluminescent or bioluminescent molecules, may also be employed.

Reference herein to an "antibody" includes parts and fragments thereof and synthetic forms thereof and extend to any immunointeractive molecule. A molecular framework is encompassed by the term "antigen" which includes antigenic portions of the molecular framework. The antigen used in according with this aspect of the present invention may be in cyclic form or it may be a linear form or precursor form thereof.

The cyclic molecular frameworks according to the present invention are useful as therapeutic agents in animals and as anti-pathogenic agents in plants.

Accordingly, the present invention provides a method for the treatment or prophylaxis of conditions or diseases in mammals, preferably humans, including the step of administering a molecular framework as hereinbefore described either without modification or having heterologous amino acids grafted thereon.

In particular, molecular frameworks may be selected or engineered for use in the treatment of neurological disorders such as acute and chronic pain, stroke, traumatic brain injury, migraine, epilepsy, Parkinson's disease, Alzheimer's disease, multiple sclerosis, schizophrenia and depression as well as cystic fibrosis and/or other respiratory diseases. The molecular framework may also be selected to treat plants against pathogen infestation and mammals including humans from viral or microbial infection.

The present invention also provides a composition comprising cyclic molecular framework molecules as hereinbefore described and a pharmaceutically acceptable carrier and/or diluent.

Preferably the composition is in the form of a pharmaceutical composition.

There is also provided the use of a cyclic molecular framework in the manufacture of a medicament for the treatment or a prophylaxis of diseases or other conditions in mammals, preferably in humans.

As will be readily appreciated by those skilled in the art, the route of administration and the nature of the pharmaceutically acceptable carrier will depend on the nature of the condition and the mammal to be treated. It is believed that the choice of a particular carrier or delivery system, and route of administration could be readily determined by a person skilled in the art. In the preparation of any formulation containing the peptide actives care should be taken to ensure that the activity of the framework is not destroyed in the process and that the framework is able to reach its site of action without being destroyed. In some circumstances it may be necessary to protect the framework by means known in the art, such as, for example, micro encapsulation. Similarly the route of administration chosen should be such that the peptide reaches its site of action. In view of the improved stability and/or bioavailability of the cyclic frameworks relative to their "linear" counterparts a wider range of formulation types and routes of administration is available.

The pharmaceutical forms suitable for injectable use include sterile injectable solutions or dispersions, and sterile powders for the extemporaneous preparation of sterile injectable solutions. They should be stable under the conditions of manufacture and storage and may be preserved against the contaminating action of microorganisms such as bacteria or fungi. The solvent or dispersion medium for the injectable solution or dispersion may contain any of the conventional solvent or carrier systems for peptide actives, and may contain, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about where necessary by the inclusion of various antibacterial and antifungal agents, for example, parabens, chlorobutanol, phenol, sorbic acid, thimerosal and the like. In many cases, it will be preferable to include agents to adjust osmollity, for example, sugars or sodium chloride. Preferably, the formulation for injection will be isotonic with blood. Prolonged absorption of the injectable compositions can be brought about by the use in the compositions of agents delaying absorption, for example, aluminum monostearate and gelatin. Pharmaceutical forms suitable for injectable use may be delivered by any appropriate route including intravenous, intramuscular, intracerebral, intrathecal injection or infusion.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredient is suitably protected, it may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated; with excipients and used in the form of ingestible tablets, buccal tablets, troches, capsules, elixirs, suspensions, syrups, wafers, and the like. Such compositions and preparations preferably contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to any other forms suitable for administration, for example, topical application such as creams, lotions and gels, or compositions suitable for inhalation or intranasal delivery, for example solutions or dry powders.

Parenteral dosage forms are preferred, including those suitable for intravenous, intrathecal, or intracerebral delivery.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form. A unit dosage form can, for example, contain the principal active compound in amounts ranging from 0.25 μg to about 2000 mg. Expressed in proportions, the active compound is generally present in from about 0.25 μg to about 2000 mg/ml of carrier. In the case of compositions containing supplementary active ingredients, the dosages are determined by reference to the usual dose and manner of administration of the said ingredients.

The cyclic molecular frameworks of the present invention may also have useful application as anti-pathogen agents in plants. Examples of pathogens include insects, spiders, viruses, fungi and other microorganisms causing deleterious effects. In particular, molecular frameworks may be engineered for use in conferring protection from pathogen (including insect) infestation of plants; for example, protection from insect attack in cotton. Such an activity may be engineered by the introduction of appropriate amino acid residues into the molecular framework, as described above, and their use in topical applications such as, e.g. in sprays.

Accordingly, the present invention provides a method for conferring pathogen protection to a plant, including the step of administering an engineered framework as hereinbefore described. Reference to administering includes reference to the topical application in liquid, aerosol, droplet, powdered or particulate form.

The present invention is exemplified herein in relation to the isolation of cycloviolacin 01 from *Viola odorata*. The preparation of uncycles is exemplified using kalata B 1 (Daly et al, 1999b). This is done, however, with the understanding that the present invention extends to all novel members of the CCK family.

The present invention is further described by the following non-limiting Examples.

EXAMPLE 1

NMR Spectroscopy

The key structural features of CCK molecules are illustrated by reference to the structure determination of cycloviolacin 01 using NMR spectroscopy and simulated annealing calculations. Samples for $^1H$ NMR measurement contained ~1.5 mM peptide in 90% v/v $H_2O$/10% v/v $D_2O$ at pH 3.6 Spectra were recorded at 290, 298 and 305 K either on a Bruker ARX-500 spectrometer equipped with a shielded gradient unit or on a Bruker DRX-750 spectrometer. The following homonuclear 2 D NMR spectra were recorded in phase-sensitive mode using time-proportional phase incrementation for quadrature detection in $t_1$:TOCSY using a MLEV-17 spin lock sequence with an isotropic mixing period of 80 ms; NOESY with mixing times of 200, 250 and 300 ms; double quantum filtered DQF-COSY and E-COSY. For DQF-COSY and E-COSY spectra solvent suppression was achieved using selective low-power irradiation of the water resonance during a relaxation delay of 1.8 s. Water suppression for NOESY and TOCSY experiments was achieved using a modified WATERGATE sequence. Spectra were acquired over 6024 Hz with 4096 complex data points in F2 and 512 increments in the F1 dimension, with 16 to 64 scans per increment. Spectra were processed on a Silicon Graphics Indigo workstation using UXNMR (Bruker) software. The $t_1$ dimension was zero-filled to 2048 real data points and 90° C. phase-shifted sine bell window functions were applied prior to Fourier transformation. Chemical shifts were referenced to DSS at 0.00 ppm. Slow exchanging amide protons were detected after the sample was lyophilized and reconstituted in 99.99% $^2H_2O$. $^3J_{H\alpha\text{-}H\beta}$ coupling constants were measured from an E-COSY spectrum and $^3J_{NH\text{-}H\alpha}$ coupling constants were measured from a DQF-COSY spectrum.

Distance restraints were derived from the 200 ms NOESY spectrum. Inter-proton distance restraints were assigned upper-distance bounds of 2.70 Å, 3.50 Å or 5.00 Å corresponding to strong, medium or weak cross-peak volumes, respectively. Pseudoatom corrections were applied where necessary to methylene and methyl protons. Backbone dihedral angle restraints were measured from either ID NMR spectra or the anti-phase cross-peak splitting in a high digital resolution 2D DQF-COSY spectrum, with $\phi$ restrained to $-65\pm15°$ for $^3J_{NH-H\alpha}$=3.0-5.8 HZ (Cys20), $-120\pm30°$ for $^3J_{NH-H\alpha}$=8.0-90.5 Hz (Ser4, Val12, Leu16, Ser21, Asn27, Ile29) and $-120\pm15°$ for $^3J_{NH-H\alpha}$>9.5 Hz (Cys5, Val24, Tyr26). Stereospecific assignment of methylene protons and $X_1$ dihedral angle restraints were derived for seven residues (Val6, Cys10, Val12, Thr13, Asn22, Val24 and Asn27) using $^3J_{H\alpha-H\beta2}$ and $^3J_{H\alpha-H\beta3}$ coupling constants measured from an E-COSY spectrum in combination with $H_N$-$H_{\beta2}$, $H_N$-$H_{\beta3}$, $H_\alpha$-$H_{\beta2}$ and $H_\alpha$-$H_{\beta3}$ NOE intensities. The two sets of $\gamma$-methyl protons of Val6, Val12 and Val24 were stereospecifically assigned based on their $H_N$-$H_\gamma$ NOE intensities and $^3J_{H\alpha-H\beta}$ values measured from a DQF-COSY spectrum. The presence of $\alpha H_{i-1}$-$\delta H_i$ NOEs and the absence of $\alpha H_{i-1}$-$\alpha H_i$ NOEs for both proline residues, Pro9 and Pro30, confirmed that their amide bonds were in the trans conformation.

Three-dimensional structures of cycloviolacin O1 were calculated using a dynamic simulated annealing protocol in the program X-PLOR version 3.1 using NMR-derived restraints as previously described (Daly et al, 1999b). Geometrical and energetic statistics for the structures are given in Table 4.

TABLE 4

Energetic statistics for the family of 20 cycloviolacin 01 structures[1]

| | |
|---|---|
| Mean pairwise r.m.s. deviations (Å)[2] | |
| Backbone | 0.58 ± 0.19 |
| Heavy atom | 1.17 ± 0.26 |
| Mean r.m.s.d. from experimental restraints | |
| NOE (Å) | 0.02 ± 0.002 |
| Dihedral angles (°) | 0.35 ± 0.06 |
| Mean r.m.s.d. from idealized covalent geometry[3] | |
| Bonds (Å) | 0.009 ± 0.0004 |
| Angles (°) | 2.27 ± 0.06 |
| Impropers (°) | 0.21 ± 0.02 |
| Mean energies (Kj/mol) | |
| $E$NOE[4] | 7.34 ± 1.40 |
| Edih[4] | 0.17 ± 0.05 |
| EL-J[5] | −117.2 ± 4.9 |
| $E$bond | 5.08 ± 0.48 |
| $E$improper | 0.83 ± 0.15 |
| $E$angle | 54.82 ± 2.96 |
| $E$total | −42.1 ± 0.40 |

[1]The values in the Table are given as mean ± standard deviation.
[2]r.m.s. deviation measured for the whole molecule.
[3]Idealized geometry as defined by CHARMm force field and as implemented within X-PLOR.
[4]Force constants for the calculation of square-well potentials for the NOE and dihedral angle restraints were 50 kcal mol$^{-1}$Å$^{-1}$ and 200 kcal mol$^{-1}$ rad$^{-2}$, respectively.
[5]The Lennard-Jones van der Waals energy was calculated with CHARMm empirical energy function.

EXAMPLE 2

Identification and Characterization of Cycloviolacin O1

Figure 7:
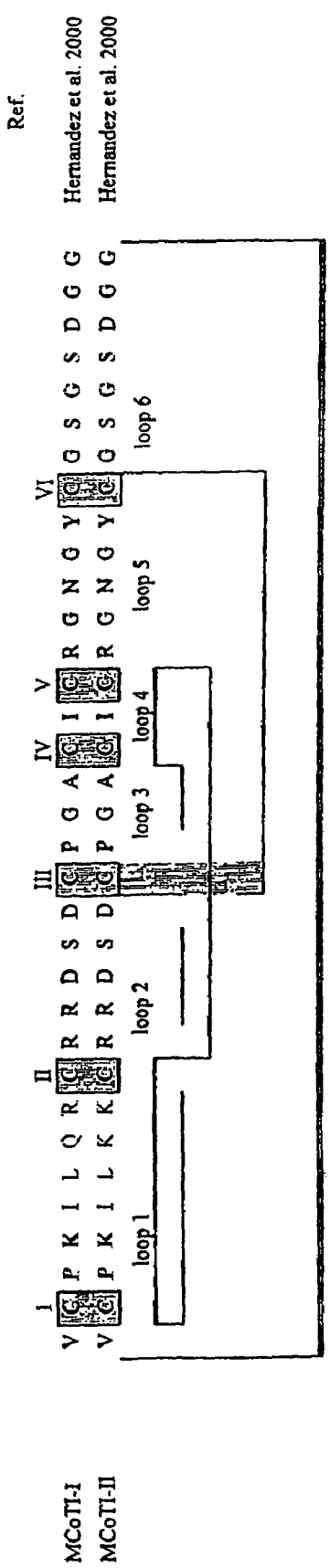
FIG. 7 is a representation of the amino acid sequences of cyclic peptides, McoTI-I (SEQ ID NO:46) and McoTI-II (SEQ ID NO:47) as described by Hernandez et al. 2000.

Based on the investigation of the prototypic macrocyclic peptide kalata B1 (Saether et al, 1995) the inventors looked for macrocyclic peptides in *Viola odorata* by screening chromatographic fractions using mass spectometry. Fresh plant material was ground and extracted with 1:1 methanol/dichloromethane. The HPLC profile of *Viola odorata* extracts prepared in this way showed a large number of peaks (FIG. 1) but the inventors focussed particularly on those with long retention times (>20 minutes). Mass spectra of these peaks were recorded and those with apparent molecular weights in the range 2500-3500 were further examined. For example, the mass spectrum of the last-eluting peak in FIG. 1 suggested a molecular mass of 3116. On reduction of the isolated fraction corresponding to this peak, six mass units were gained, suggesting the possibility of six cysteine residues being present. Amino acid sequence of this fraction yielded the sequence shown in FIG. 1, which is consistent with the molecular weight derived from mass spectometry. All of these available evidence suggest that the naturally occurring peptide is the head-to-tail cyclic derivative of this sequence, which the inventors refer to as "cycloviolacin O1", reflecting its origin as the first macrocyclic peptide characterised from *V. odorata*. A range of macrocyclic peptides of similar mass have been found in *V. hederaceae*, *V. betonicifolia* and *O. affinis*. A selection of the derived sequences is shown in Table 5 and it is clear that the family of cyclic peptides is very widespread in plants. To facilitate the study of such peptides and their comparisons with other molecules the inventors refer to this generic family of macrocyclic peptides as the plant "cyclotides", defined here to include peptides of ~30 amino acids with a cyclized backbone and six cysteine residues involved in three disulfide bonds. Another useful source of cyclic peptides is from cucurbitaceae plants (e.g. *Momordica cochinchinensis*) [Hernandez et al, 2000]. A representation of the amino acid sequences of two cyclic peptides from *M. cochinchinensis* is shown in FIG. 7.

Methods

Cycloviolacin 01 was isolated from aerial parts of *Viola odorata*, harvested in Brisbane, Australia by extraction with dichloromethane/methanol (50:50 v/v) and purified using reverse phase HPLC (Vydac C18 column) on a Waters HPLC System. Gradients of CH$_3$CN in H$_2$O (0.1% trifluoroacetic acid, v/v) were employed in the purification. Cycloviolacin 01 (molecular weight 3116) was reduced with an excess of TCEP and alkylated with maleimide. The reduced and alkylated peptide was cleaved with Endo-Glu C in NH$_4$Ac buffer at pH 8 for 1-2 hours and then purified by reverse phase HPLC. The cleaved peptide was N-terminally sequenced using Edman degradation on an Applied Biosystems 477A Protein Sequencer.

TABLE 5

Sequence alignment of cyclic cystine knot peptides from Rubiaceae and Violaceae species

| | I | II | III | IV | V | VI | | |
|---|---|---|---|---|---|---|---|---|
| cycloviolacin 01 (SEQ ID NO:1) | . C | A E S C | V Y I P C | T V T A L L G C | S C | . S N R V C | Y . N G . I P | this work |
| cycloviolacin 02 (SEQ ID NO:2) | . C | G E S C | V W I P C | I S S A . I G C | S C | . K S K V C | Y R N G . I P | this work |
| cycloviolacin 03 (SEQ ID NO:3) | . C | G E S C | V W I P C | L T S . A I G C | S C | . K S K V C | Y R N G . I P | this work |
| cycloviolacin 04 (SEQ ID NO:4) | . C | G E S C | V W I P C | I S S A . I G C | S C | . K N K V C | Y R N G . I P | this work |
| cycloviolacin 05 (SEQ ID NO:5) | . C | G E S C | V W I P C | I S S . A V G C | S C | . K N K V C | Y K N G T . P | this work |
| cycloviolacin 06 (SEQ ID NO:6) | . C | G E S C | V W I P C | I . S A A V G C | S C | . K S K V C | Y K N G T L P | this work |
| cycloviolacin 07 (SEQ ID NO:7) | . C | G E S C | V W I P C | T I T A L A G C | K C | . K S K V C | Y . N S . I P | this work |
| cycloviolacin 08 (SEQ ID NO8) | . C | . E S C | V W I P C | I S S . V V G C | S C | . K S K V C | Y K N G T L P | this work |
| cycloviolacin 09 (SEQ ID NO:9) | . C | G E S C | V W I P C | L T S A V . G C | S C | . K S K V C | Y R N G . I P | this work |
| cycloviolacin 010 (SEQ ID NO:10) | . C | G E S C | V Y I P C | L T S A V . G C | S C | . K S K V C | Y R N G . I P | this work |
| cycloviolacin 011 (SEQ ID NO:11) | . C | G E S C | V W I P C | I . S A V V G C | S C | . K S K V C | Y K N G T L P | this work |
| cycloviolacin H1 (SEQ ID NO:12) | . C | G E S C | V Y I P C | L T S A . I G C | S C | . K S K V C | Y R N G . I P | this work |
| kalata B5 (SEQ ID NO:13) | . C | G E S C | V Y I P C | I S G V I . G C | S C | . T D K V C | Y L N G T . P | this work |
| circulin A (SEQ ID NO:14) | . C | G E S C | V W I P C | I . S A A L G C | S C | . K N K V C | Y R N G . I P | Gustafson et al., 1994 |
| circulin B (SEQ ID NO:15) | . C | G E S C | V F I P C | I S T . L L G C | S C | . K N K V C | Y R N G V I P | Gustafson et al., 1994 |
| cyclopsychotride A (SEQ ID NO:16) | . C | G E S C | V F I P C | . V T A L L G C | S C | . K S K V C | Y K N S . I P | Witherup et al., 1994 |

| | | | | | | | | |
|---|---|---|---|---|---|---|---|---|
| violapeptide 1 (SEQ ID NO:17) | V C | G E T C | V G G T C | . . . N T P G C | S C | . S R P V C | T X N G . L P | Schöpke et al., 1993 X=R? |
| kalata B1 (SEQ ID NO:18) | V C | G E T C | V G G T C | . . . N T P G C | T C | . S W P V C | T R N G . L P | Saether et al., 1995 |
| kalata B2 (SEQ ID NO:19) | V C | G E T C | F G G T C | . . . N T P G C | S C | . T W P I C | T R D G . L P | this work |
| kalata B3 (SEQ ID NO:20) | T C | G E T C | F G G T C | . . . N T P G C | T C | D P W P I C | T R D G . L P | this work |
| kalata B4 (SEQ ID NO:21) | V C | G E T C | V G G T C | . . . N T P G C | T C | . S W P V C | T R D G L P | this work |
| varv peptide A (SEQ ID NO:22) | V C | G E T C | V G G T C | . . . N T P G C | S C | . S W P V C | T R N G . L P | Claeson et al., 1998 |
| varv peptide B (SEQ ID NO:23) | V C | G E T C | F G G T C | . . . N T P G C | S C | D P W P M C | S R N G . L P | Göransson et al., 1999 |
| varv peptide C (SEQ ID NO24) | I C | G E T C | V G G T C | . . . N T P G C | S C | . S W P V C | T R N G V . P | Göransson et al., 1999 |
| varv peptide D (SEQ ID NO:25) | I C | G E T C | V G G S C | . . . N T P G C | S C | . S W P V C | T R N G . L P | Göransson et al., 1999 |

TABLE 5-continued

Sequence alignment of cyclic cystine knot peptides from Rubiaceae and Violaceae species

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| varv peptide E (SEQ ID NO:26) | I | C | G | E | T | C | V | G | G | T | C | . | . | . | N | T | P | G | C | S | C | . | S W P V | C | T R N G . L | P | Göransson et al., 1999 |
| varv peptide F (SEQ ID NO:27) | I | C | G | E | T | C | T | L | G | T | C | . | . | . | Y | T | A | G | C | S | C | . | S W P V | C | T R N G V . | P | Göransson et al., 1999 |
| varv peptide G (SEQ ID NO:28) | V | C | G | E | T | C | F | G | G | T | C | . | . | . | N | T | P | G | C | S | C | D | P W P V | C | S R N G V . | P | Göransson et al., 1999 |
| varv peptide H (SEQ ID NO:29) | V | C | G | E | T | C | F | G | G | T | C | . | . | . | N | T | P | G | C | S | C | E | T W P V | C | S R N G . L | P | Göransson et al., 1999 |
| | | loop 1 | | | | | loop 2 | | | | | loop 3 | | | | | | | | | | loop 4 | | | loop 6 | | | |

EXAMPLE 3

Three-Dimensional Structure of Cycloviolacin 01

750 MHZ NMR spectra of cycloviolacin 01 were recorded, assigned and used to determine the three-dimensional structure of this peptide. The cyclic nature of cycloviolacin 01 was unequivocally confirmed by a continuous closed series of sequential NOE connectivities, including dαN, dNN or dαδ in the case of Pro. The three-dimensional structure is shown in FIG. 2 and illustrates the compact fold of the molecule which contains a number of β-turns, three β-strands arranged in a triple-stranded β-sheet, a short helical segment, and a network of disulfide bonds which form a cystine knot (Mc-Donald et al, 1993; Isaacs, 1995; Pallaghy et al, 1994; Norton and Pallaghy, 1988). The cystine knot consists of an embedded ring in the structure, formed by two disulfide bonds and their connecting peptide backbones, which is penetrated by the third disulfide bond. In the case of cycloviolacin 01 the embedded ring is an octapeptide, made up of disulfide-linked tri- and penta-peptide backbone segments. The cystine knot motif is seen in other larger proteins (murray-Rust, 1993) although the size of the embedded ring is larger than in the case of the cyclotides and so the impression of a knot is not so apparent. Consideration of van der Waals radii suggests that an octapeptide ring is the smallest hole through which a disulfide bond could penetrate.

EXAMPLE 4

The Cyclic Cystine Knot is a Conserved Structural Framework Amongst the Cyclotide Family of Peptides From the conserved spacing of cysteine residues across the family of cyclotides, the inventors considered that the other members of the family would adopt similar three-dimensional structures, and to confirm this, the inventors compared cycloviolacin 01 to kalata B1 (Saether et al, 1995) and circulin A (Daly et al, 1999b), the only other macrocyclic peptides for which structures have been determined. The global folds of cycloviolacin 01, kalata B1 and circulin A were shown to be similar, with the RMS fit over backbone atoms of the loops with conserved spacing being <1.3 Å for all three molecules.

Figure 2A:
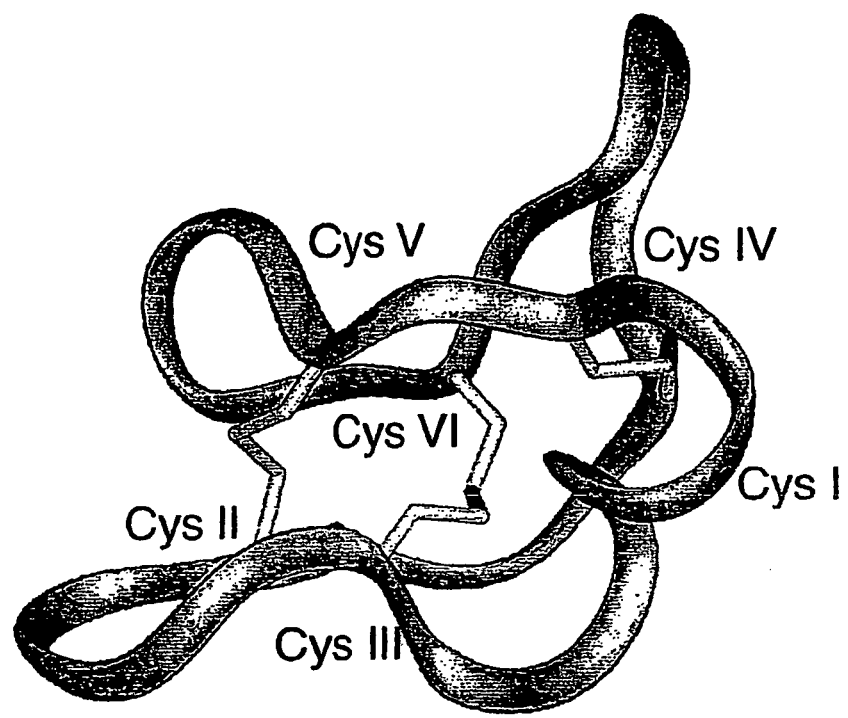
FIG. 2 is a diagrammatic representation showing the structural features of cycloviolacin 01 and other plant cyclotides. (a) A ribbon representation of the NMR-derived structure of cycloviolacin 01, with the cysteine residues numbered $Cys^I$ to $Cys^{VI}$. (b) A superimposition of the cystine-knots of kalata B1, circulin A and cyloviolacin 01. Only the cystine residues are shown and their Cα atoms are highlighted as spheres. (c) A schematic representation of the cyclic cystine knot motif showing the arrangement of the connected disulfide bonds and the general topology of the knot. The bold arrows represent the strands of the β-hairpin (labelled strand 1 and strand 2) and the shaded arrow represents an extended region which is distorted from standard β-geometry but nominally makes up the third strand of the β-sheet. (d) A summary of the conserved and variable residues in the known cyclotides. The conserved amino acids involved in the formation of the embedded ring in the structure are outlined in grey and connected by disulfide bonds $Cys^I$-$Cys^{IV}$ and $Cys^V$-$Cys^{II}$. All other amino acids are outlined in black, with variable residues shaded with diagonal lines and conserved residues in plain circles. In an attempt to represent something of the three-dimensional topography of the knot, those residues closer to the observer are outlined with a thicker black outline.
Figure 2B:
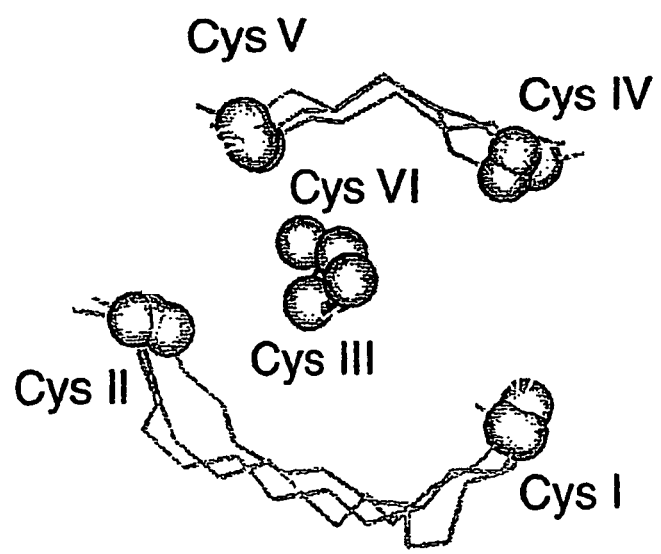
Figure 2C:
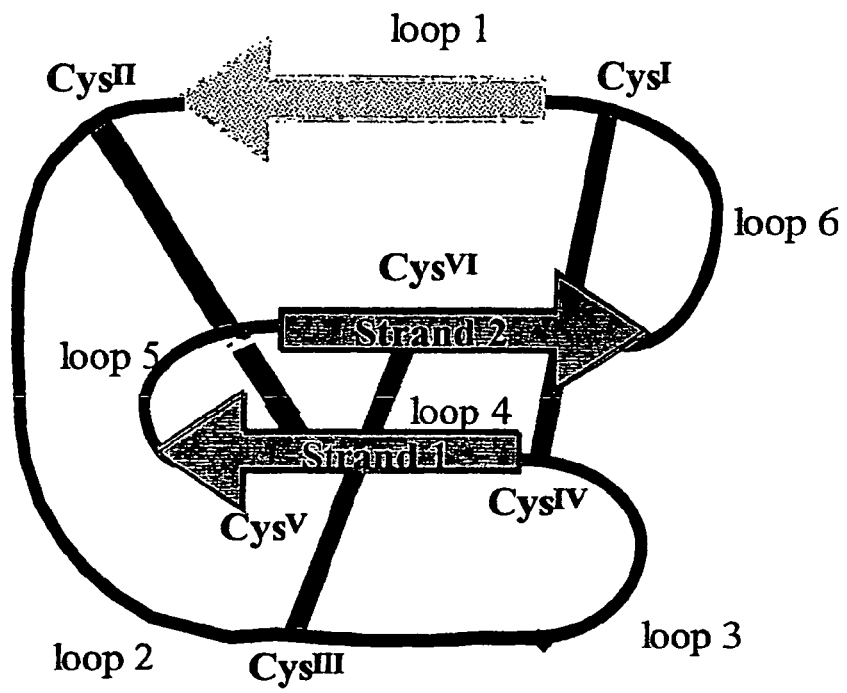

The fit is particularly close over the cystine knot core of the molecules, as shown in FIG. 2b. It is clear that these molecules form a consensus structure, which the inventors refer to as the cyclic cystine knot (CCK). The main elements of this new protein motif are shown in FIG. 2c. Two of the β-strands form a hairpin which is essentially at the core of the knot, containing three of the six Cys residues. The two strands of the hairpin are linked with several hydrogen bonds. The third strand is distorted from ideal β geometry, and contains a β-bulge in the segment between $Cys^I$ and $Cys^{II}$.

The determination of the sequences of an extensive series of macrocyclic peptides, together with three-dimensional structures of three members of the family, allows some general conclusions to be drawn regarding the role of particular amino acids in defining the knotted topology. Table 5 includes the sequences of the new cyclotide peptides identified by the inventors in the course of developing the instant invention together with various peptides reported previously from the Violaceae and Rubiaceae plant families. The alignments are based on the six highly conserved Cys residues whose disulfide connectivity is indicated schematically at the bottom of the Table. This representation shows the embedded ring formed by two intracysteine backbone segments and their connecting disulfide bonds, $Cys^I$-$Cys^{IV}$ and $Cys^{II}$-$Cys^V$, and highlights the penetration of this ring by the third disulfide bond ($Cys^{III}$-$Cys^{VI}$). Because of the cyclic nature of the amide backbone, there are nominally six loops (i.e., six separate backbone segments) between successive Cys residues, and these are numbered loop 1 to loop 6 at the bottom of the Table. Their topological placement is illustrated in FIG. 2c. Examination of the sequences shows that there is remarkable conservation amongst many of the loops, but for those loops where there are variations, the peptides fall into two subfamilies:

Loops 1 and 4 correspond to the backbone segments of the embedded ring of the cystine knot and are the most conserved part of the sequence. Loop 1 comprises residues GET/S (the third residue is S in subfamily 1 and T in sub-family 2), while loop 4 contains just a single residue, most often S.

Loop 2 contains exactly four residues, but has different compositions in the two sub-families. In sub-family 1, the first three residues are hydrophobic and the fourth residue is always P. In sub-family 2, the two central residues are GG, the first residue is hydrophobic and the final residue is T, with one exception.

In loops 3 and 5 there is more variability in the number and type of residues present. For sub-family 1, loop 3 includes up to seven residues, largely hydrophobic apart from a conserved G, while in sub-family 2, there are only four residues (NTP, plus the conserved G). Loop 5 contains four or five residues, with a conserved V at the C-terminal position. Sub-family 1 contains two positively charged residues, whereas sub-family 2 contains predominantly a SWP sequence before the conserved V.

Finally, loop 6 has a C-terminal proline preceded by the sequence NGI/L, all of these residues being highly conserved. In sub-family 1, the proline is immediately adjacent to the $Cys^I$, whereas in sub-family 2 there is an intervening hydrophobic residue.

Figure 2D:
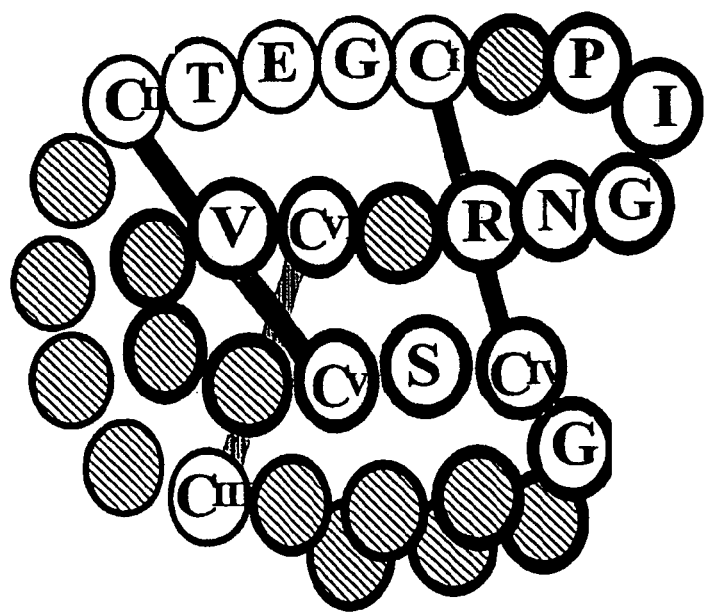
Figure 4:
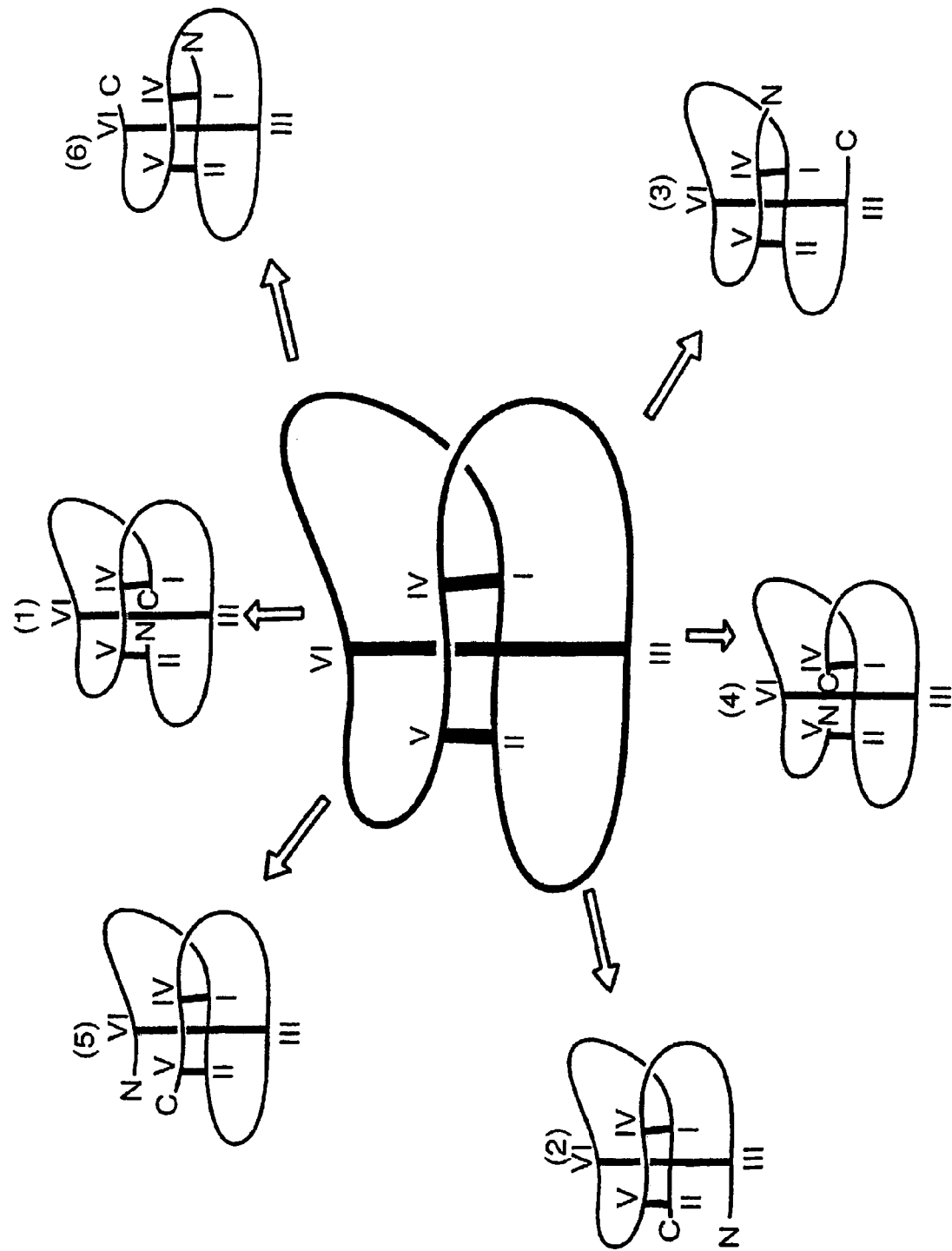
FIG. 4 is a schematic representation of the three-dimensional structure of kalata B1 (Saether et al, 1995) [middle of diagram] and the 6 acyclic permutants produced upon opening of the 6 loops between the cysteine residues. The numbers in parentheses represent the loops which are opened.
Figure 5:
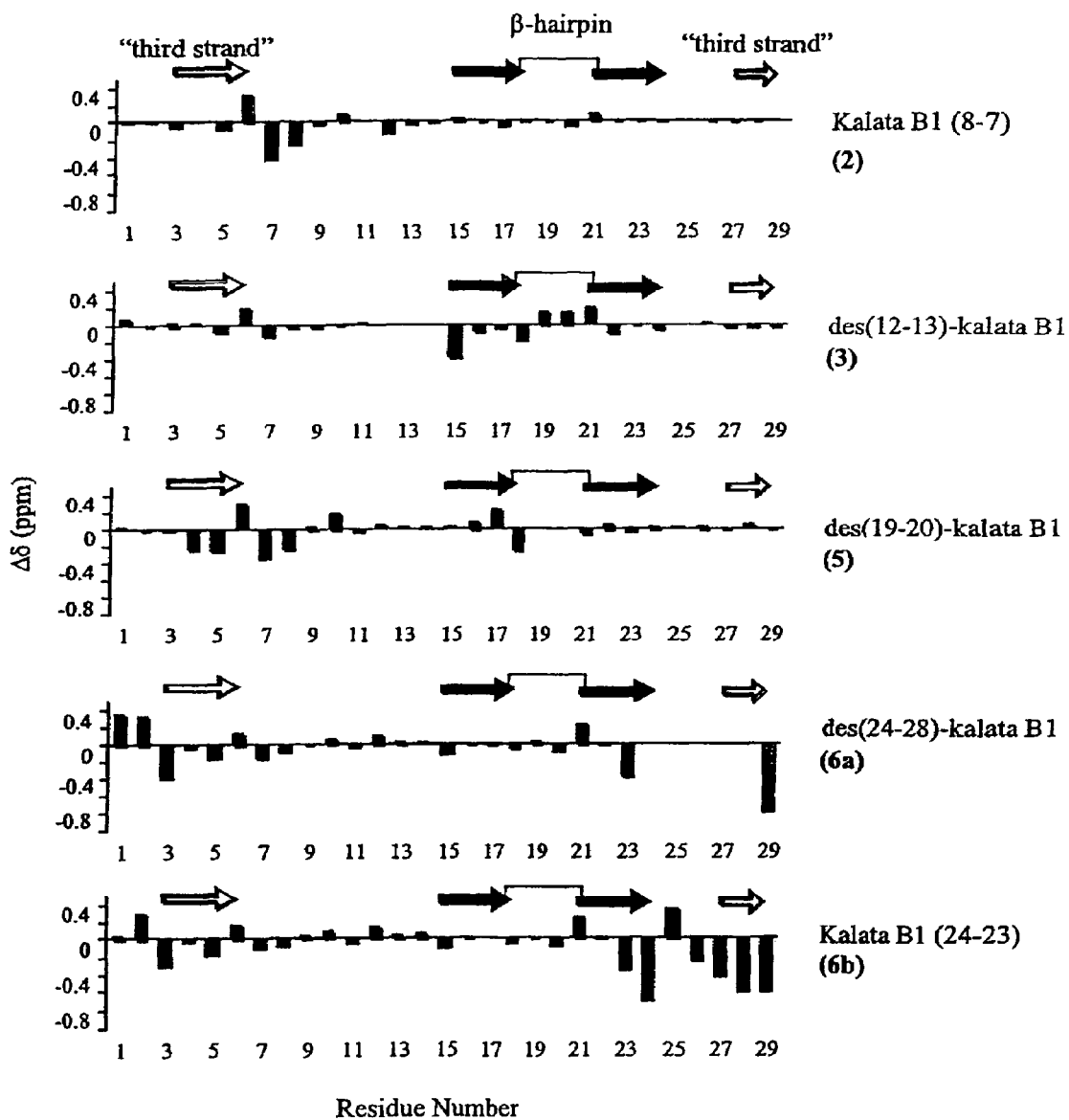
FIG. 5 is a schematic representation showing αH chemical shift difference between the acyclic permutants of kalata B and native kalata B1. Only the four permutants which produced late eluting peaks were analyzed. The chemical shifts were measured from TOCSY spectra recorded on a Bruker ARX 500 MHZ spectrometer at 298 K and are referenced to internal DSS. Arrows above the shift represent the secondary structure; the black arrows represent the β-hairpin and the white arrows represent the distorted strand which has a β-bulge present.

FIG. 2d summarizes the conserved and variable residues of the CCK motif of the cyclotide family and shows their positioning with respect to the core cystine knot. The highly conserved nature of the amino acids within the embedded ring of the cystine knot (loops 1 and 4) suggests that it is not just the number of amino acids in this motif, but their nature which stabilizes the knot. By contrast, most variability occurs in loops 2, 3 and 5. The variable residues in loops 2 and 5 are clustered together in two R-turns immediately adjacent to each other. This means that the variable residues point out into the solvent, suggesting the possibility that this region may be important in binding interactions and biological function of the cyclotides. Loop 3 varies most in size of any of the loops and this results in the only significant difference in three-dimensional structures of the different cyclotides. In sub-family 2, exemplified by kalata B1 this four residue loop forms a relatively disorded extended strand, but in sub-family 1, it is sufficiently long to form two turns of $3_{10}$-helix. This small helical segment is apparent in FIG. 2 in cycloviolacin 01. In this case, the structure has a remarkable resemblance to plant defensin structures (Broekaert et al, 1993), which consist of a triple stranded β-sheet and a single helix, suggesting a possible defence role for the cyclotides. This is further supported by the finding that cycloviolacin 01 and other CCK peptides are haemolytic agents, and cause 50% lysis of erythrocytes at a concentration of ~20 μM.

EXAMPLE 5

Topological Implications of the CCK Motifin Protein Structures

Many small cystine-rich proteins, including proteinase inhibitors from plants (Savel et al, 1998), toxins from cone snail (Nielsen et al, 1996) and spider (Narasinhan et al, 1994) venoms, and a virulence gene products such as AVR9 (Vervoort et al, 1997) from fungi adopt a cystine knot structure. This motif is thus represented in diverse species from animals, plants and fungi. The order of connectivity of disulfide bonds is similar in all of these molecules, i.e. $Cys^I$-$Cys^{IV}$, $Cys^{II}$-$Cys^V$ and $Cys^{III}$-$Cys^{VI}$, as illustrated in FIG. 3a. However, the spacing of amino acids between cysteine residues is generally such that the apparent knot in the structures is much looser than in the cyclotides. In addition, there is a fundamental topological difference between the cyclic and acyclic cystine knot proteins. Although commonly referred to as knots, the latter are in fact not knotted in a mathematical sense, are topologically simple, and may be drawn in two dimensions on a non-crossing diagram, such as is shown in FIG. 3b. By contrast, the cyclotides are topologically complex, cannot be represented without crossing in a planar diagram (FIG. 3c), and may thus be regarded as true knots. It is interesting to note that backbone cyclization is a necessary, but not sufficient, condition for knotting as described here, because it is possible to envisage cyclic disulfide-rich proteins such as that represented in FIG. 3d, which are not knotted.

The issue of whether there are knots in proteins is complicated by different usage of the term. "knot". For example, a typical representation of the fold of many "cystine knot" proteins is shown in FIG. 3e. On the basis of common usage it is intuitively reasonable to refer to such structures as knotted, however, they may clearly be untied by a non-bond-breaking geometrical transformation, as illustrated in the series FIGS. 3e-h, with structure 3h exemplifying the topologically simple nature of these molecules, equivalent to 3b. In this example, the untying involves pushing the C-terminus and its associated peptide chain through the embedded ring in the middle of the knot as shown. Although such an unthreading mechanism at first seems unlikely, it has been suggested that this may indeed be responsible for a very slow unfolding of human nerve growth factor (De Young et al, 1996).

Such unthreading, or the reverse process of threading to form the cystine knot, is clearly not possible in CCK proteins such as the cyclotides, because they do not have an N- or C-terminus. Formation of the knot must arise from successive formation of individual disulfide bonds, with the central penetrating bond presumably not formed last as this would seem sterically unfavourable. Cyclization presumably occurs enzymatically. It is of interest to note that closing the ends of an untied knot via cyclization can, in principle, be done in one of several topologically distinct ways, leading to topological chirality. For example, joining of the N- and C-termini of FIG. 3h could occur either over, or under the intervening backbone, leading to topological isomers. In the cyclotides for which the inventors have determined structures, only one of the possible topological isomers occurring naturally is observed.

EXAMPLE 6

The Cyclic Cystine Knot as a Molecular Engineering Framework

The cyclotides have exceptional stability as demonstrated, for example, by the fact that in one medical application African women boil the plant containing kalata B1 and drink it, implying a high degree of chemical and enzymatic stability, as well as oral bioavailability. The inventors have tested a wide range of proteases for activity against cyclotides and find that the oxidized CCK framework is completely impervious to enzymatic cleavage. This may be consistent with the compact three-dimensional structures shown in FIG. 2. Protease digestion is only possible after reduction of the disulfide bonds to remove the cystine knot. The stability of this framework indicates that it is useful as an engineering scaffold onto which different amino acid sequences can be grafted to achieve different functional ends. Applications include pharmaceuticals or agrochemicals.

EXAMPLE 7

Synthesis of Kalata B1 with Loops 2 and 4 of MVIIA Grafted onto the Framework

MVIIA is a non-cyclic disulfide rich peptide which has potential therapeutic applications for the treatment of pain. The loops of MVIIA (Olivera et al, 1987) thought to be essential for activity (loops 2 and 4) have been grafted onto the CCK framework of kalata B1. The inventors have achieved this by replacing two of the β-turns of kalata B1 with the relevant sequences from MVIIA. The consensus structure of the CCK framework shows that these turns are not part of the knotted core or the triple stranded β-sheet which is the major structural element of this class of peptide. The sequence of the synthetic peptide is shown below:—

Loop 4 Loop 2

CTCRSGKCTRNGLPVCGETCSRLMYDCNTPG (SEQ ID NO:38)

Oxidation of the reduced cyclic material is achieved by placing peptide (approx. 0.5 mg/ml) in a buffer such as 0.1 M ammonium carbonate pH 7.8, in the presence of guanadinium chloride and reduced glutathione (1 mM). The reaction is allowed to proceed at room temperature for approximately 24 hours. The disulfide isomers are purified by reverse phase HPLC.

The residues in bold represent loops 2 and 4 of MVIIA which were inserted into the cyclic sequence of kalata B 1. The sequence was synthesized as shown above with an N-terminal cysteine and a C-terminal glycine residue. Cyclization was achieved via a C-terminal thioester reacting with the N-terminal cysteine residue. There are five other potential sites for cyclization via the remaining cysteine residues, however, this site was chosen because the proceeding residue is a glycine, in contrast to the other sites, and thus steric problems during cyclization would be minimized. The synthesis was performed on a Boc-Gly-$SCH_2CH_2CO$ Gly PAM resin. The linker was attached to the Gly-PAM resin by treating the resin with bromopropanoic acid for 30 minutes, washing with DMF and then treating the resin with 10% v/v thioacetic acid, 10% v/v DIEA in DMF for 2×20 minutes. The resin was again washed with DMF and treated with 10% v/v 16-mercaptoethanol, 10% v/v DIEA in DMF for 2×20 minutes. After a final wash with DMF, Boc-glycine was coupled to the resin using HBTU and DIEA. The peptide was assembled by manual synthesis using HBTU with in situ neutralization.

The disulfide bonds are formed by disolving the peptide in 0.1 M ammonium bicarbonate (pH 7.8), 50% v/v isopropanol and 1 mM reduce glutathione. The reaction was left at room temperature for 3 days and the peptide subsequently purified with reverse phase HPLC on a semi-preparative C18 column.

EXAMPLE 8

Generation of Acyclic Permutants of Kalata B1

Permutants of kalata B1 were assembled using manual solid phase peptide synthesis with Boc chemistry on a 0.5 mmole scale. MBHA or PAM resin was used (Applied Biosystems, Foster City, Calif.) and amino acids added to the resin using HBTU with in situ neutralization (Schnolzer et al, 1992). N-teminal acetylation was performed on resin for one of the permutants with a vast excess of acetic anhydride and DIEA in DMF. Cleavage of the peptide from the resin was achieved using hydrogen fluoride (HF) with cresol and thiocresol as scavengers (HF:cresol:thiocresol; 9:1:1 v/v). The reaction was allowed to proceed at −5° C. for 1 hour. Following cleavage, the peptides were dissolved in 50% v/v acetonitrile, 0.1% v/v TFA and lyophilized. The crude, reduced peptides were purified using preparative reverse-phase HPLC (RP-HPLC) on a Vydac C18 column. Gradients of 0.1% v/v aqueous TFA and 90% v/v acetontrile/0/09% v/v TFA were employed with a flow rate of 8 mL/min and the eluant monitored at 230 nm. These conditions were used in the subsequent purification steps. Mass analysis was performed on a Sciex (Thornhill, Ontario) triple quadrupole mass spectrometer using electrospray sample ionization.

Oxidation reactions were performed using the conditions established for the cyclic peptide (Daly et al, 1999a). The purified reduced peptides were dissolved in 50% v/v isopropanol, 1-10 mM reduced glutathione in 0.1 M ammonium bicarbonate (pH 8.5). The reactions were left a room temperature for 24 hours. The pH was lowered with TFA prior to purification with RP-HPLC.

There are six cysteine residues in the CCK molecules and hence six loops in the backbone which can be opened to form six possible topologically distinct acyclic permutants. The inventors synthesized a series of truncated acyclic permutants of kalata B1 in which each of the six loops was opened to examine the effects these changes had on folding, structure and activity. A schematic representation of the acyclic permutants is given in FIG. 4. In general, the permutants were designed to include one residue either side of the cysteines and the intervening residues deleted. However, in some cases a single residue was deleted or the permutants contain the entire amino acid sequence but are acylic. The sequences and nomenclature of the seven permutants synthesized are given in Table 6 and the numbering system used is based on that in Daly et al (1999b).

All permutants, with the exception of kalata B1, were synthesized on MBHA resin to produce a C-terminal amide upon cleavage with HF. The N-termini of the permutants are positively charged. However, des(12-13)-kalata B1 was also synthesized with an acetylated N-terminus to examine the effect the positive charge on the N-terminus has in the activity studied. Kalata B1 was synthesized with a free C-terminus to allow cyclization.

The permutants of kalata B1 were assembled using manual solid phase peptide synthesis and subsequently purified using RP-HPLC prior to oxidation. The oxidation conditions were chosen based on the previous studies on the synthesis of kalata B1 which revealed that cyclic, reduced kalata B1 folds very efficiently in 0.1 M ammonium bicarbonate (pH 8), 1 mM reduced glutathione in 50% v/v isopropanol at room temperature. Applying these oxidation conditions to the folding of the kalata B1 permutants enabled a comparison of the efficiency of folding and allowed the effect of opening the loops of the molecule to be assessed.

To further examine the conformation present in the late eluting peaks they were purified by RP-HPLC and studied with $^1H$ NMR spectroscopy. TOCSY and NOESY spectra were recorded and resonance assignments were obtained using established techniques (Wuthrich, 1986). Chemical shifts are extremely sensitive to structural changes and thus an analysis of the chemical shifts was used to compare the structures of the permutants. The αH chemical shifts of the permutants were compared to that of the native peptide (FIG. 5). When loops 1 and 4 are perturbed, the peptide does not fold into the native structure. However, it is apparent from FIG. 5, that the permutants shown in this diagram have similar shifts to the native peptide indicating the overall three-dimensional structure is retained. In general, the major differences are near the termini, however, other differences also exist. The most significant differences observed are in kalata B1 where loop 6 is opened and no longer appears to be restrained as judged by chemical shifts which are much closer to random coil than the native peptide.

An analysis of αH chemical shifts are routinely used for comparing structures, however, an analysis of βH chemical shifts can also be informative for comparing side chain conformations. The chemical shift difference between β-protons of the AMX spin systems have been measured for the permutants and compared to the values observed for the native peptide. Des-12-13)-kalata B1, kalata B8-7) and des-19-20)-kalata B1 have very similar trends to the native peptide for residues 11-26. However, there are more significant differences in cysteine residues 1, 5 and 10. Kalata B1-(24-23) and des-24-28)-kalata B13 also display differences for residues 1, 5 and 10.

Assays were performed in 12×75 mm borasilicate culture tubes at room temperature and incubated for 1 hr. Each tube contained 100 ml each of test compound, iodinated ligand (7 fmol) and rat membrane (16 mg) added in this order. The assay buffer contained 20 mM HEPES pH 7.2, 75 mM NaCl, 0.1 mM EDTA, 0.1 mM EGTA, 0.1° 1% w/v BSA and protease inhibitors, 2 mM leupeptin and 0.5 U aprotinin. The non-specific binding was determined in the presence of either 17 nM GVIA or 100 nM MVIIC. Assays were terminated by

TABLE 6

Acyclic permutants of kalata B1[a]

```
      1        5        10       15       20       25          Native kalata B1
      ┌─CGETCVGGTCNTPGCTCSWPVCTRNGLPV─┐ (SEQ ID NO:30)

-CG    TCVGGTCNTPGCTCSWPVCTRNGLPV-(SEQ ID NO:31)   Des-(3)-kalata B1       (1)
-CGETCVGGTCNTPGCTCSWPVCTRNGLPV-(SEQ ID NO:32)      Kalata B1-(8-7)         (2)
-CGETCVGGTCN   GCTCSWPVCTRNGLPV-(SEQ ID NO:33)     Des(12-13)-kalata B1    (3)
-CGETCVGGTCNTPGC    CSWPVCTRNGLPV-(SEQ ID NO:34)   Des(16)-kalata B1       (4)
-CGETCVGGTCNTPGCTCS   VCTRNGLPV-(SEQ ID NO:35)     Des(19-20)-kalata B1    (5)
-CGETCVGGTCNTPGCTCSWPVCT      V-(SEQ ID NO:36)     Des(24-28)-kalata B1    (6a)

┌─CGETCVGGTCNTPGCTCSWPVCTRNGLPV─┐ (SEQ ID NO:37) Kalata B1-(24-23)      (6b)
   └┘ └┘ └┘    └┘    └┘
   loop1 loop2 loop3  loop5 loop6
                loop 4
```

[a]The native sequence is backbone cyclized. The N- and C- termini of the acyclic permutants are highlighted in bold. The nomenclature chosen describes the residues deleted or in the case of the full length, non-cyclic permutants the residue numbers of the N- and C- termini are in parentheses. The numbers in parentheses following the name of the permutant refers to the loop which is perturbed with des(23-38)-kalata B1 and kalata B1(24-23) designated 6a and 6b, respectively.

EXAMPLE 9

Binding of New Grafted Analog to N-Type Calcium Channels

Antagonists specific to N-type voltage-sensitive calcium channels are being used as leads in drug development. Examples of these are ω-conotoxins GVIA and MVIIA. An assay has been previously established to determine the ability of a compound to displace 125I-GVIA from receptors in rat membrane. Rat membrane was prepared according to the procedure of Wagner et al, 1988. Rats were sacrificed by cervical dislocation and their brains removed and immediately frozen in liquid nitrogen. Frozen brains were stored at −78° C. until required. Three brains (wet weight, 6.25 g) were thawed (50 mM HEPES, pH 7.4) and homogenized with ultraturrex (IKA, 170 Watt) in 125 ml 50 mM HEPES pH 7.4. Homogenized brain was centrifuged at 16000 rpm (35000 g) for 20 min at 4° C. and the supernatant discarded. The pellet was resuspended by further homogenization in 50 mM HEPES, pH 7.4, 10 mM EDTA and incubated at 4° C. for 30 min. Centrifugation was repeated as above and the supernatant discarded. The pellet was resuspended in 125 mls 50 mM HEPES, pH 7.4 (1:20 dilution) and stored at −78° C.

125I-[Tyr22]GVIA was prepared according to the procedure of Cruz and Olivera (1986) and isolated by reverse-phase HPLC on an analytical Vydac C18 column. The column was equilibrated in buffer A ($H_2O$, 0.1% v/v TFA) followed by a linear gradient to 67% buffer B (90% v/v acetonitrile, 10% v/v $H_2O$ and 0.09% v/v TFA) in 100 min. Peaks were detected at 214 nm and the flow rate was 1 ml/min. The radiolabeled peaks were counted using a gamma counter and stored at 4° C.

vacuum filtration on a Millipore manifold filtration system using glass fibre filters (Whatman GFB) presoaked in 0.6% v/v polyethylenimine. Each tube was washed 3 times with 3 ml ice-cold wash buffer (20 mM HEPES pH 7.2, 125 mM NaCl and 0.1% w/v BSA). Filters were counted on a gamma counter. Graphpad Prism was used to generate binding curves and calculate EC50 values. The EC50 values are a measure of the ability of a compound to displace $^{125}$I-GVIA; the EC50 for MVIIA is 4.4×10-11 M. The EC50 is determined for the new grafted analog using the assay as described above.

EXAMPLE 10

Grafting Platelet Inhibition Activity onto the CCK Framework

Kalata B1 has been used as an example of the CCK framework and the biologically active sequence, RGD, has been grafted onto this framework. The sequence of the grafted peptide is shown below:—

CTCRGDVCTRNGLPVCGETCVGGTCNTPG (SEQ ID NO:39)

The synthesis was achieved using solid phase peptide synthesis methods, using a thio-ester linker to facilitate cyclization. The linear peptide was purified using RP-HPLC and subsequently cyclized in ammonium bicarbonate 0.1 M pH 8 with an excess of TCEP for 2 hours at room temperature. The cyclic reduced peptide was oxidized in 50% v/v isopropanol, 0.1 M ammonium bicarbonate pH 8 in the presence of 1 mM reduced glutathione. The reaction was left overnight at room temperature and the major product purified by RP-HPLC.

Figure 6:
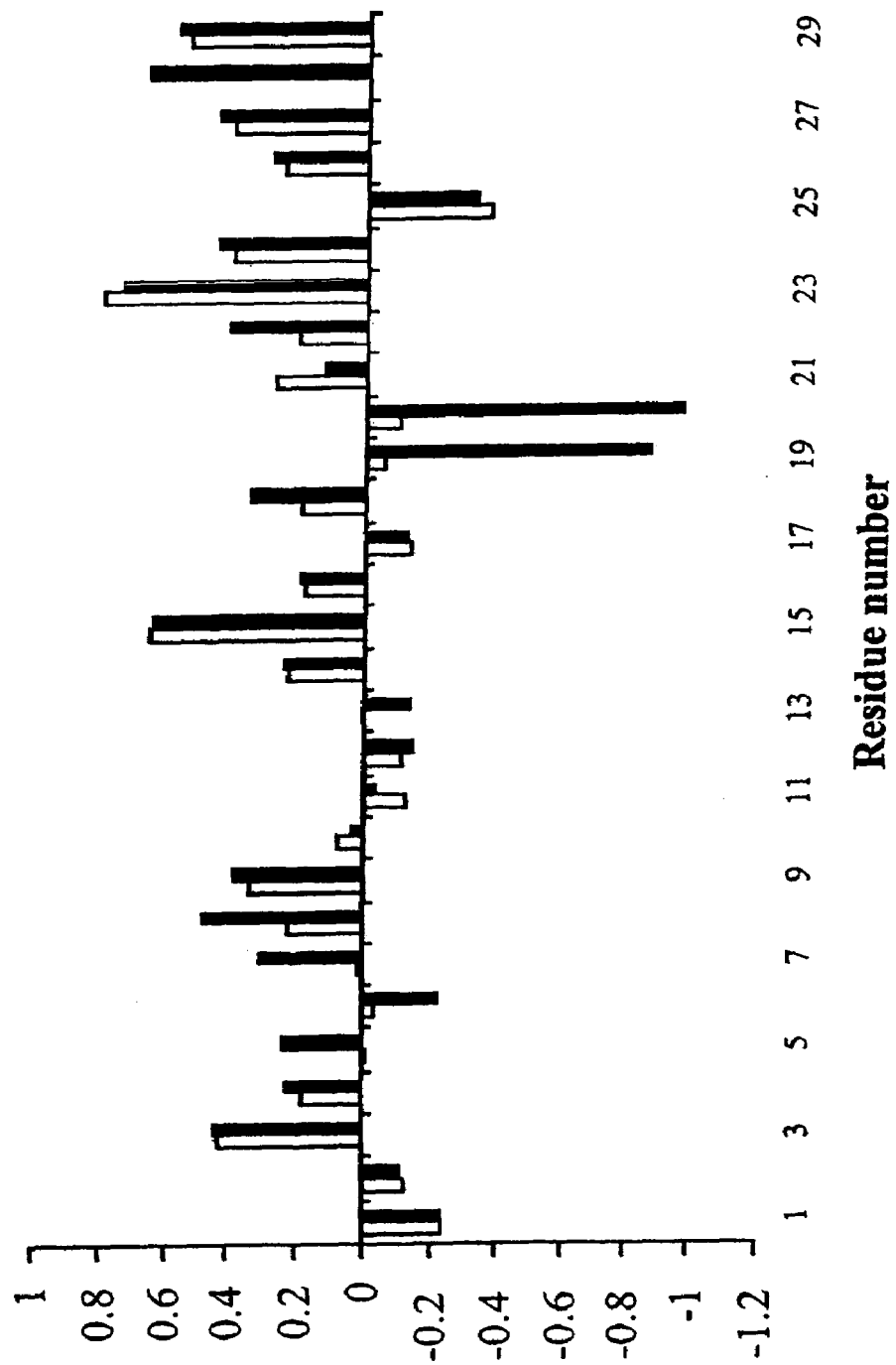
FIG. 6 is diagrammatic representation of the secondary chemical shifts of the grafted RGD peptide (open bars) and the native peptide (black bars).

Two-dimensional NMR spectra were recorded on the purified product and the individual amino acid assignments were determined using established techniques. An analysis of the chemical shifts reveals that the overall fold of the grafted peptide is very similar to that of the native peptide, indicating that despite the changes to the native sequence the inventors were able to produce a fully folded grafted peptide. The chemical shift analysis is shown in FIG. 6. Residues which are not close to the grafted sequence are not perturbed, indicating that the three-dimensional fold of the framework is not perturbed when a new sequence is grafted into it. Biological activity of the grafted analog is determined using a platelet aggregation assay well known in the art.

EXAMPLE 11

Platelet Aggregation Assay

The activity of grafted peptides designed with RGD sequences is analyzed using a platelet aggregation assay. Human blood is obtained from healthy donors who have not taken any medications within the previous 10 days. Blood is drawn into tubes containing sodium citrate, centrifuged and the platelet rich plasma transferred. Platelet aggregation is conducted at 37° C. in an aggregometer. The extent of platelet aggregation is determined by the addition of platelet aggregators such as ADP and collagen. To analyze the effect of the peptides on platelet aggregation, a solution of peptide is incubated with the platelet rich plasma prior to addition of the platelet aggregators. The extent of inhibition is determined by comparison with the maximal aggregation achieved with the control substances (ADP or collagen).

EXAMPLE 12

Grafting Protease Inhibitory Activity unto the CCK Framework

The loop which confers protease inhibitory activity to the squash family of protease inhibitors is grafted into the sequence of kalata B1 as shown below:—

CTCSWPVCTRNGLPVCPKILKKCVGGTCNTPG (SEQ ID NO:40)

The synthesis and purification is using the methods as described in Example 7. NMR spectroscopy, as described in other Examples in this specification, is used for structural analysis and comparison with the native structure.

Chromogenic substrates are used to determine the protease inhibitory activity. The peptide is preincubated with trypsin for 15 min at 25° C. prior to addition of the appropriate chromogenic substrate for trypsin (e.g. S2302 (250 µM; DiaPharma)). Absorbance changes at 405 nm are monitored over five minutes. A comparison with and without the peptide allows a determination of the extent of trypsin inhibitory activity.

EXAMPLE 13

Grafting New Serine Protease Activities onto Mco TI-II

Dengue viruses cause severe epidemics of diseases such as dengue fever and dengue hemorrhagic fever. Dengue virus type 2 (Den2) is the most prevalent of the four known serotypes. The viral genome is a single positive strand RNA that encodes a single protein precursor. The viral viability is underscored by the activity of the dengue virus NS3 serine protease (Krishna Murthy et al, 1999) that helps liberate the individual viral proteins from the precursor. Specific inhibition of this enzyme may provide a method of therapy for diseases caused by Dengue viruses. The sequence containing an in vivo cleavage site for a substrate of the Den2 protease (Krishna Murthy et al, 1999) is grafted into the sequence of McoTI-II[(Hernandez et al, 2000), changing its activity from a trypsin inhibitor to an inhibitor of the Den2 protease as shown below, with the putative cleavage site underlined:—

CICRGNGYCGSGSDGGVCKKRSWPCRRDSDCPGA (SEQ ID NO:41)

The synthesis and purification is achieved as described in Example 7 (see also FIG. 7). NMR spectroscopy is used for structural analysis and comparison with the native structure. Methods for testing the activity of NS3 proteases are well known in the art. Details of an exemplary procedure for measuring NS3 inhibitory activity by measurement of enzyme-induced hydrolysis of peptide-based fluoregenic substances is given in International Patent Publication No. WO 00/20400.

EXAMPLE 14

Grafting of G Protein-Coupled Receptor Modulatory Activity onto the CCK Framework The melanocortin receptor family which consists of 5 members (MC1-R-MC5-R) represent a subgroup of the G protein-coupled receptors. Compounds that modulate the activity of melanocortin receptors may be useful in neurological disorders, pigmentation disorders, behavioral disorders, cardiovascular disorders, metabolic disorders, sexual dysfunction and in the amelioration of inflammatory events (Oosterom et al, 1999; Adan et al, 1999).
(i) The four residue sequence, His-D-Phe-Arg-Trp, is likely to form a β-turn and forms part of the active pharmacophore of a series of peptides which modulate the activity of melanocortin receptors (Adan et al, 1999). Kalata B1 has been used as a framework and this four residue sequence is grafted onto the kalata framework. The sequence of the grafted peptide is shown below:—

CTCHD-FRWCTRNGLPVCGETCVGGTCNTPG (SEQ ID NO:42)

(ii) The five residue sequence, His-D-Phe-Arg-Trp-Asn, incorporates the β-turn described above plus an extra residue found in the melanocortin superagonist MT-II (Adan et al, 1999). Kalata B1 has been used as a framework and this five residue sequence is grafted onto the kalata framework. The sequence of the grafted peptide is:—

CTCHD-FRWNCTRNGLPVCGETCVGGTCNTPG (SEQ ID NO:43)
|_____|

The synthesis and purification is achieved as described in Example 7. NMR spectroscopy will be used for structural analysis and comparison with the native structure. The peptide agonist/antagonist activity is determined using HEK 293 cells transfected with MC1-R-MC5-R receptors as described in Adan et al, (1999) or Chen (1995).

EXAMPLE 15

Grafting of C5a-Modulatory Activity onto the CCK Framework

The C5a-receptor belongs to the family of G protein-coupled receptors. Over expression or underregulation of the C5a-receptor is implicated in a number of inflammatory conditions including rheumatoid arthritis, with potential therapies for these conditions found in the use of antagonists or agonists to the C5a-receptor (Fairlie et al. (1999) and references therein).

(i) The sequence of one C5a-receptor inhibitor (Fairlie et a2, 1999) is grafted onto loop5 of Kalata B1 as shown below:

(SEQ ID NO:44)
CTC[AcF]OPD-[Chexa]WRCTRNGLPVCGETCVGGTCNTPG
|_____|

Where AcF represents N-methyl phenylalanine, Chexa represents cyclohexylalanine and 0 represents ornithine.

(ii) The same sequence is grafted onto loop 3 of circulin A as shown below:—

(SEQ ID NO:45)
CSCKNKVCYRNGIPCGESCVWIPC[AcF]OPD-[Chexa]WR
|_____|

The synthesis and purification of both peptides is achieved as described in Example 7. NMR spectroscopy is used for structural analysis and comparison with the native structure. Activity is determined using methods described in Fairlie et al, (1999).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Adan et al., Melanocortin receptor ligands. International Patent Publication No. WO 99/54358
Benham and Jafri, *Protein Science* 2: 41-54, 1993.
Broekaert et al, *Plant Physiol.* 108: 1353-1358, 1995.
Chen et al, *Anal. Biochem* 226: 349-354, 1995.
Cruz and Olivera, *J. Biol. Chem.* 262: 6230-6233, 1986.
Claeson et al, *Journal of Natural Products* 61: 77-81, 1998.
Daly et al, *Biochemistry* 38: 10606-10614, 1999a
Daly et al, *J. Mol. Biol.* 285: 333-345, 1999b.
Douillard and Hoffman, Basic Facts about Hybridomas, in *Compendium of Immunology Vol. II, ed by Schwartz*, 1981.
Fairlie et al, International Patent Publication No. WO 99/00406.
Favel et al, *Int. J. Pept. Pro. Res.* 33: 202-208, 1988.
Göransson et al, *Journal of Natural Products* 62: 283-286, 1999.
Gustafson et al, *J. Am. Chem. Soc.* 116: 9337-9338, 1994.
Hernandez et al, *Biochemistry* 39: 5722-5730, 2000.
Issacs et al, *Current Opinion in Structural Biology* 5: 391-395, 1995.
Kohler and Milstein, *European Journal of Immunology* 6: 511-519, 1976.
Kohler and Milstein, *Nature* 256: 495499, 1975;
Krishna et al, *J. Biol. Chem.* 274: 5573-5580, 1999.
McDonald et al, *Cell* 73: 421424, 1993.
Murray-Rust et al, *Structure* 1: 153-159, 1993.
Narasimhan et al, *Natural Structural Biology* 1: 850852, 1994.
Nielsen et al, *J. Mol. Biol.* 263: 297-310, 1996.
Norton et al, *Toxicon* 36: 573-583, 1998.
Olivera et al, *Biochemistry* 26: 2086-2090, 1987.
Oosterom et al, *J. Biol. Chem* 274: 16853-60, 1999.
Pallaghy et al, *Protein Science* 3: 1833-1839, 1994.
Saether et al, *Biochemistry* 34: 41474158, 1995.
Schnolzer et al, *Int. J. Pept. Protein Res.* 40: 180-193, 1992.
Schopke et al, *Sci. Pharm.* 61: 145-153, 1993.
Vervoort et al, *FEBS Letts.* 404: 153-158, 1997.
Witherup et al, *Journal of Natural Products* 57: 1619-1625, 1994.
Wüthrich et al, *Proteins and Nucleic Acids*, 1986.

The invention claimed is:

1. A method of preparing a proteinaceous molecule having a cyclic cystine knot backbone and with a defined biological activity, comprising:

a) providing:

i) an amino acid sequence of a peptide, wherein said peptide comprises a plurality of contiguous amino acids and has a defined biological activity, and wherein said peptide is about 2 to about 30 amino acid residues; and ii) an assay for detecting said defined biological activity;

b) preparing a proteinaceous molecule having a cyclic cystine knot backbone by grafting the amino acid sequence of said peptide of step a) onto a cyclic cystine knot framework wherein said cyclic cystine knot backbone comprises the structure:

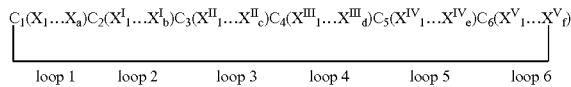

$$C_1(X_1 \ldots X_a)C_2(X^I_1 \ldots X^I_b)C_3(X^{II}_1 \ldots X^{II}_c)C_4(X^{III}_1 \ldots X^{III}_d)C_5(X^{IV}_1 \ldots X^{IV}_e)C_6(X^V_1 \ldots X^V_f)$$

loop 1 loop 2 loop 3 loop 4 loop 5 loop 6 wherein $C_1$ to $C_6$ are cysteine residues;

wherein each of $C_1$ and $C_4$, $C_2$ and $C_5$, and $C_3$ and $C_6$ are connected by a disulfide bond to form a cystine knot;

wherein each X represents an amino acid residue in a loop, wherein said amino acid residues may be the same or different;

wherein d is about 1-2;

wherein one or more of loops 1, 2, 3, 5 or 6 have an amino acid sequence comprising the sequence of said peptide of step a), wherein any loop comprising said sequence of said peptide of step a) comprises 2 to about 30 amino acids, and wherein for any of loops 1, 2, 3, 5, or 6 that do not contain said sequence of said peptide of step a), a, b, c, e, and f, may be the same or different, a may be any number from 3-10, and b, c, e, and f may be any number from 1 to 20; and c) exposing said proteinaceous molecule having a cyclic cystine knot backbone to said assay to identify a proteinaceous molecule having a cyclic cystine knot backbone and having said defined biological activity.

2. The method according to claim 1, wherein said amino acid sequence of said peptide of step a) comprises a portion of an amino acid sequence of a larger protein, wherein said peptide confers said defined biological activity on said larger protein.

3. The method according to claim 1, wherein for any of loops 1, 2, 3, 5, or 6 that do not contain said sequence of said peptide of step a), a is from about 3 to 6, b is from about 3 to about 5, c is from about 2 to about 7, e is from about 3 to about 6 and f is from about 4 to about 9.

4. The method according to claim 1, wherein a is about 3 and d is about 1, wherein for any of loops 2, 3, 5, or 6 that do not contain said sequence of said peptide of step a), b is about 4, c is from about 4 to about 7, e is about 4 or 5 and f is from about 4 to about 7.

5. The method according to claim 1, wherein a is about 6 and d is about 1, wherein for any of loops 2, 3, 5, or 6 that do not contain said sequence of said peptide of step a), b is about 5, c is about 3, e is about 5 and f is about 8.

6. The method of claim 1, wherein any loop comprising said sequence of said peptide of step a) comprises 2 to about 20 amino acids.

7. The method of claim 1, wherein any loop comprising said sequence of said peptide of step a comprises 2 to about 10 amino acids.

8. The method of claim 1, wherein said peptide of step a) is a peptide selected from the group consisting of Loop 2 and Loop 4 of MVIIA, a protease inhibitor, a Den2 protease inhibitor, a G Protein-coupled receptor modulator, and a C5a-receptor modulator.

9. The method of claim 1, wherein said defined biological activity is selected from the group consisting of N-type voltage-sensitive calcium channel antagonist activity, protease inhibitory activity, Den2 protease inhibitory activity, G Protein-coupled receptor modulator activity, and C5a-receptor modulator activity.

* * * * *

UNITED STATES PATENT AND TRADEMARK OFFICE
CERTIFICATE OF CORRECTION

PATENT NO.       : 7,687,457 B2                               Page 1 of 1
APPLICATION NO.  : 11/120501
DATED            : March 30, 2010
INVENTOR(S)      : David James Craik et al.

It is certified that error appears in the above-identified patent and that said Letters Patent is hereby corrected as shown below:

Title Page, Item (75) Inventors, delete the second "o" from Norello and insert --e-- in its place. Also delete "s" from Clements.

Column 62, line 28, add ")" after the word "a" and before the word "comprises.".

Signed and Sealed this

Eleventh Day of May, 2010

David J. Kappos
*Director of the United States Patent and Trademark Office*